US007016786B1

(12) United States Patent
Ranganathan et al.

(10) Patent No.: US 7,016,786 B1
(45) Date of Patent: Mar. 21, 2006

(54) STATISTICAL METHODS FOR ANALYZING BIOLOGICAL SEQUENCES

(75) Inventors: Rama Ranganathan, Dallas, TX (US); Steve W. Lockless, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 0 days.

(21) Appl. No.: 09/684,066

(22) Filed: Oct. 6, 2000

Related U.S. Application Data

(60) Provisional application No. 60/157,974, filed on Oct. 6, 1999.

(51) Int. Cl.
 *G01N 33/48* (2006.01)
 *G06F 19/00* (2006.01)
(52) U.S. Cl. ......................................... 702/19; 702/20
(58) Field of Classification Search ................... 702/19
 See application file for complete search history.

(56) References Cited

U.S. PATENT DOCUMENTS 5,523,208 A   6/1996   Kohler et al. .................. 435/6

OTHER PUBLICATIONS

Altschul et al., "Gapped BLAST and PSI-BLAST: a new generation of protein database search programs," *Nucl. Acids Res.*, 25(17):3389-3402, 1997.
Atwell et al., "Structural plasticity in a remodeled protein-protein interface," *Science*, 278:1125-1128, 1997.
Bailey and Gribskov, "Combining evidence using p-values: application to sequence homology searches," *Bioinformatics*, 14(1):48-54, 1998.
Böhm and Jaenicke, "Correlation functions as a tool for protein modeling and structure analysis," *Protein Science*, 1:1269-1278, 1992.
Cabral et al., "Crystal structure of a PDZ domain," *Nature*, 382:649-652, 1996.
Carter et al., "The use of double mutants to detect sturctural changes in the active site of the Tyrosyl-tRNA synthetase (*Bacillus stearothermophilus*)," *Cell*, 38:835-840, 1984.
Clackson and Wells, "A hot spot of binding energy in a hormone-receptor interface," *Science*, 267:383-386, 1995.
Daniels et al., "Crystal structure of the hCASK PDZ domain reveals the structure basis of class II PDZ domain target recognition," *Nat. Struct. Biol.*, 5(4):317-325, 1998.
Doyle et al, "Crystal structures of a complexed and peptide-free membrane protein-binding domain: molecular basis of peptide recognition by PDZ," *Cell*, 85:1067-1076, 1996.
Heim and Tsien, "Engineering green fluorescent protein for improved brightness, longer wavelengths and fluorescence resonance energy transfer," *Curr. Biol.*, 6:178-182, 1996. Article printed from the BioMedNet website, http://journals.bmn.com/journals/list/browse . . . Jan. 8, 2002.

Feng and Doolittle, "Progressive alignment of amino acid sequences and construction of phylogenetic tress from them, " *Meth. Enzymology*, 266:368-382, 1996.
Goldstein et al., "The charybdotoxin receptor of a Shaker $K^+$ channel: peptide and channel residues mediating molecular recognition," *Neuron*, 12:1377-1388, 1994.
Hedstrom et al., "Converting trypsin to chymotrypsin: the role of surface loops," *Science*, 255:1249-1253, 1992.
Hedstrom, "Trypsin: a case study in the structural determinants of enzyme specificity," *Biol. Chem.*, 377:465-470, 1996.
Hidalgo and MacKinnon, "Revealing the architecture of $K^+$ channel pore through mutant cycles with a peptide inhibitor, " *Science*, 268:307-310, 1995.
Holt and Ackers, "The pathway of allosteric control as revealed by hemoglobin intermediate states," *FASEB J.*, 9:210-218, 1995.
Hughey and Krogh, "Hidden Markov models for sequence analysis: extension and analysis of the basic method," *Comput. Appl. Biosci.*, 12(2):95-107, 1996.
Karlin and Brendel, "Chance and statistical significance in protein and DNA sequence analysis," *Science*, 257:39-49, 1992.
Karlin, "Statistical significance of sequence patterns in proteins," *Curr. Opin. Struct. Biol.*, 5:360-371, 1995.
Karlin, "Statistical studies of biomolecular sequences: score-based methods," *Philos. Trans. R. Soc. Lond. B. Biol. Sci.*, 344:325-402, 1994.
Leluk, "A new algorithm for analysis of the homology in protein primary structure," *Comput. Chem.*, 22(1):123-131, 1998.
LiCata and Ackers, "Long-range, small magnitude nonadditivity of mutational effects in proteins," *Biochemistry*, 34(10):3133-3139, 1995.

(Continued)

*Primary Examiner*—Marjorie A. Moran
*Assistant Examiner*—Lori A. Clow
(74) *Attorney, Agent, or Firm*—Fulbright & Jaworski L.L.P.

(57) ABSTRACT

Statistical algorithms that are useful to aid in the identification of evolutionarily conserved amino acid positions within a family of proteins, and in the identification of interacting amino acid positions within a protein sequence are disclosed. The algorithms may also be useful in the analysis of other polymer sequences such as polysaccharides, lipids, deoxyribonucleic acid (DNA), and ribonucleic acid sequences (RNA), and, more specifically, in the analysis of DNA microarray data. Algorithms useful for analyzing the structural changes of perturbations to determine the mechanisms by which positions are coupled are also disclosed.

14 Claims, 12 Drawing Sheets

OTHER PUBLICATIONS

Lichtarge et al., "An evolutionary trace method defines binding surfaces common to protein families," *J. Mol. Biol.*, 257:342-358, 1996.

Lockless and Ranganathan, "Evolutionarily conserved pathways of energetic connectivity in protein families," *Science*, 286:295-299, 1999.

Monod et al., "On the nature of allosteric transitions: a plausible model," *J. Mol. Biol.*, 12:88-118, 1965.

Nicholls, et al., "Protein folding and association: insights from the interfacial and thermodynamic properties of hydrocarbons," *Proteins*, 11:281-296, 1999.

Ortiz et al., "Method for low resolution prediction of small protein tertiary structure," *Pacific Symp. On Biocomputing*, 316-327, 1997.

Patten et al., "The immunological evolution of catalysis," *Science*, 271:1086-1091. 1996.

Perona et al., "Structural origins of substrate discrimination in trypsin and chymotrypsin," *Biochemistry*, 34:1489-1499, 1995.

Perry et al., "Long-range electrostatic interactions can influence the folding, stability, and cooperativity of dihydrofolate reductase," *Biochemistry*, 28:7961-7968, 1989.

Pettigrew et al., "Probing the energetics of proteins through structural perturbation: sites of regulatory energy in human hemoglobin," *Proc. Natl. Acad. Sci. USA*, 79:1849-1853, 1982.

Ponting et al., "PDZ domains: targeting signalling molecules to sub-membranous sites," *BioEssays*, 19(6):469-479, 1997.

Ranganathan et al., "Spatial localization of the $K^+$ channel selectivity filter by mutant cycle-based structure analysis," *Neuron*, 16;131-139, 1996.

Sambrook et al., *Molecular Cloning: A Laboratory Manual*, 2$^{nd}$ Ed., Cold Spring Harbor, NY, 1989.

Schreiber and Fersht, "Energetics of protein—protein interactions: analysis of the Barnase—Barstar interface by single mutations and double mutant cycles," *J. Mol. Biol.*, 248:478-486, 1995.

Songyang et al., "Recognition of unique carboxyl-terminal motifs by distinct PDZ domains," *Science*, 275:73-77, 1997.

Stampe et al., "Intimations of $K^+$ 3channel structure from a complete functional map of the molecular surface of charybdotoxin," *Biochemistry*, 33:433-450, 1994.

Stroud and Fauman, "Significance of structural changes in proteins: expected errors in refined protein structures," *Protein Sci.*, 4:2392-2404, 1995.

Sunyaev et al., "PSIC: profile extraction from sequence alignments with position-specific counts of independent observations," *Protein Eng.*, 12(5):387-394, 1999.

Thompson et al., "CLUSTAL W: improving the sensitivity of progressive multiple sequence alignment through sequence weighting, position-specific gap penalties and weight matrix choice," *Nucl. Acids Res.*, 22(22):4673-4680, 1994.

Tolman, *The principles of statistical mechanics*, Dover Publications Inc., New York, 1938.

Turner et al., "Mutagenic dissection of hemoglobin cooperativity: effects of amino acid alteration on subunit assembly of Oxy and Deoxy tetramers," *Proteins*, 14;333-350, 1992.

Vingron and Waterman, "Sequence alignment and penalty choice. Review of concepts, case studies and implications," *J. Mol. Biol.*, 235:1-12, 1994.

Wells, "Binding in the growth hormone receptor complex," *Proc. Natl. Acad. Sci. USA*, 93;1-6, 1996.

Wells, "Structural and functional epitopes in the growth hormone receptor complex," *Bio/Technol.*, 13:647-651, 1995.

STATISTICAL METHODS FOR ANALYZING BIOLOGICAL SEQUENCES

BACKGROUND OF THE INVENTION

This application claims priority to provisional patent application Ser. No. 60/157,974 filed Oct. 6, 1999, entitled "Statistical Method for Measuring the Energetic Properties of Proteins Through Sequence Analysis." The entire text of the above-referenced disclosure is specifically incorporated by reference herein without disclaimer.

The Appendix to this specification contains computer-program source code that is the property of the assignee. Copies of the source code may be made as part of making facsimile reproductions of this specification, but all other rights in the source code are reserved. Those with skill in the art having the benefit of this disclosure will understand that the appended source code may be modified as necessary for use with operating systems other than the standard, UNIX-based operating system for which it is currently written. For example, the appended source code may be modified for use with any Microsoft Windows operating system.

1. Field of the Invention

The invention relates generally to analyzing biological sequences. This invention relates more particularly to methods for analyzing biological sequences using algorithms, which sequences include, but are not limited to, proteins, ribonucleic acids (RNA), deoxyribonucleic acids (DNA), lipids, and polysaccharides (sugars).

2. Description of Related Art

The ability of all cells to recognize their environment and to make appropriate responses to stimuli depends on the organized activity of networks of proteins that we conventionally refer to as the cellular signal transduction machinery. These protein networks show remarkable signal processing properties such as the ability to extract small signals from noise and to adjust their sensitivity to changes in background stimulation while preserving excellent specificity. As used herein, "specificity" is the ability of proteins or protein networks to selectively respond to one stimulus in the background of other potentially competing stimuli. Defects in signaling proteins are commonly the basis for many human diseases, highlighting the need for a fundamental understanding of the mechanisms of signal recognition and processing.

The basic paradigm of signaling involves the sequential establishment of molecular interactions and the allosteric control of enzyme activities. At an atomic level, these processes reduce to the orderly flow of energy within and between proteins whose structural basis is not generally well understood. For example, the effect of ligand binding at extracellular sites in a transmembrane receptor molecule presumably propagates via the motion of coupled structural elements to induce functional changes in intracellular domains and the subsequent interaction with downstream target proteins. The interaction of one protein with another can be thought of as an energetic perturbation to each binding surface that propagates through the three-dimensional structure to cause specific changes in protein function (Holt, J. M. and Ackers, G. K., Faseb J 9: 210–218, 1995; Monod, J. et al., J. Mol. Biol. 12: 88–118, 1965; Perry, K. M. et al., Biochem. 28: 7961–7968, 1989; Pettigrew, D. W. et al., Proc. Natl. Acad. Sci. U.S.A. 79: 1849–1853, 1982; LiCata, V. J. and Ackers, G. K., Biochemistry 34: 3133–3139, 1995; Turner, G. J. et al., Proteins 14: 333–350, 1992). The structural basis of this energy propagation is largely unknown, but is likely to be critical in understanding the relationship between protein function and structure.

At specific protein—protein interfaces, large-scale mutagenesis together with structure determination has begun to define some features of energy parsing. (As used herein, "energy parsing" describes the way that energy is parceled out amongst the amino-acid residues at a particular protein—protein interface. Mutagenesis is a method of generating DNA-level changes to a gene encoding a protein in order to change the identity of an amino acid at a chosen position on the protein.) For example, studies of the interaction of human growth hormone with its receptor show that binding energy is not smoothly distributed over the interaction surface; instead, a few residues comprising only a small fraction of the interaction surface account for the majority of the free energy change (Atwell, S. et al., Science 278: 1125–1128, 1997; Clackson, T. and Wells, J. A., Science 267: 383–386, 1995; Wells, J. A., Proc. Natl. Acad. Sci. U.S.A. 93: 1–6, 1996; J. A. Wells, Biotechnol. 13: 647–651, 1995).

Similarly, potassium channel pores interact with peptide scorpion toxins with high affinity, but most of the binding energy depends on two amino acid positions on the toxin molecule though fifteen residues are likely buried upon binding (Goldstein, S. A. et al., Neuron 12: 1377–1388, 1994; Hidalgo, P. and MacKinnon, R., Science 268: 307–310, 1995; Ranganathan, R. et al., Neuron 16: 131–139, 1996; Stampe, P. et al., Biochemistry 33: 443–450, 1994). Thus, protein interaction surfaces contain functional epitopes or "hot spots" of binding energy that are generally not predictable from the atomic structure.

In addition, a large body of evidence suggests that the change in free energy at a protein interaction surface propagates through the tertiary structure in a seemingly arbitrary manner. For example, studies addressing mechanisms of substrate specificity in serine proteases show that many positions distantly positioned from the active site contribute to determining the energetics of catalytic residues (Hedstrom, L., Biol. Chem. 377: 465–470, 1996; Hedstrom, L. et al., Science 255: 1249–1253, 1992; Perona, J. J. et al., Biochemistry 34: 1489–1499, 1995).

Indeed, the conversion of trypsin to chymotrypsin specificity required a large set of simultaneous mutations, many at unexpected positions. Similarly, mutations introduced during maturation of antibody specificity have been shown to occur at sites distant in tertiary structure from the antigen-binding site despite substantial increases in binding energy (Patten, P. A. et al., Science 271: 1086–1091, 1996). Thus, protein function appears to depend on the energetic interactions of a set of amino acid positions that are structurally dispersed and that, like binding hot spots, are unpredictable from even high-resolution crystal structures.

One potential approach to mapping these energetic interactions in a protein is through massive mutagenesis. Indeed, thermodynamic mutant cycle analysis (Hidalgo, P. and MacKinnon, R., Science 268: 307–310, 1995; Carter, P. J. et al., Cell 38: 835–840, 1984; Schreiber, G. and Fersht, A. R., J. Mol. Biol. 248: 478–486, 1995), a technique that measures the energetic interaction of two mutations, provides a direct method to systematically probe energetic relationships of protein sites. However, practical considerations, such as the number of mutants that can be reasonably generated and studied per unit time in the laboratory, limit this technique to small-scale studies, obviating a full mapping of all energetic interactions on a complete protein.

Statistical methods have been reported for the analysis of biological sequences, typically in the determination of homologous protein families and evolutionary conservation.

Ortiz, A. R. et al. (*Pac. Symp. Biocomput.*, 316–327, 1997) describes a method of predicting the low resolution three dimensional structure of proteins starting from a multiple sequence alignment. Secondary structure predictions and minimized Monte Carlo energy calculations are used to predict protein structures.

Sunyaev, S. R. et al. (*Protein Eng.*, 12: 387–394, 1999) describes the use of position-specific independent counts at a given position in a sequence alignment in identifying distantly related protein sequences.

Karlin, S. and Brendel, V. (*Science*, 257: 39–49, 1992) discuss the use of statistical methods for characterizing anomalies in sequences, for determining compositional biases in proteins, and for analyzing spacings of sequence markers. Karlin (*Curr. Opin. Struct. Biol.*, 5: 360–371, 1995; *Philos. Trans. R. Soc. Lond. B. Biol. Sci.* 344: 391–402, 1994) further describes the use of statistical methods for the identification of common segments between protein sequences, and the use of distributional theory in multiple sequence alignments.

Bailey, T. L. and Gribskov, M. (*Bioinformatics*, 14: 48–54, 1998) propose the use of the QFAST statistical algorithm for accurate and sensitive sequence homology searches.

Hughey, R. and Krogh, A. (*Comput. Appl. Biosci.* 12: 95–107, 1996) discuss the use of Hidden Markov models (HMMs) to identify protein sequences with a given domain, or to perform a multiple alignment of sequences.

Vingron, M. and Waterman, M. S. (*J. Mol. Biol.* 235: 1–12, 1994) describe statistical analyses of DNA and protein alignments. Statistics are used to optimize alignment parameters.

Leluk, J. (*Comput. Chem.* 22(1):123–131, 1998) describes statistical analyses of proteins taking advantage of the correlation between amino acids and their corresponding DNA codons. The analyses are useful for determining corresponding sequences between proteins, and for investigating evolutionary divergence between proteins.

Bohm, G. and Jaenicke, R. (*Protein Sci.* 1: 1269–1278, 1992) propose the use of statistical methods for the discrimination between native protein three dimensional structures and corresponding misfolded structures.

U.S. Pat. No. 5,523,208 (issued Jun. 4, 1996) discusses the use of amino acid hydropathy values to search protein databases for proteins predicted to interact with each other.

The foregoing shows that a need exists for improved methods for the identification of evolutionarily-conserved and interacting positions in biological sequences, such as interacting amino acid positions in protein sequences. The identification of evolutionarily-conserved amino acid positions may be used to identify key regions in the protein for protein-drug interactions, to identify potential sites in proteins that lead to hereditary mutation diseases, and the identification of catalytic sites to improve enzyme activities, to name but several examples. The identification of interacting amino acid positions is useful to predict how a protein folds into a three dimensional structure, to predict how distant sites may interact to form a catalytic active site in an enzyme, and to predict effects of a drug interaction with an amino acid position may affect other amino acid positions, to name but a few examples.

SUMMARY OF THE INVENTION

The invention relates to a statistical method for the analysis of biological sequences. The invention is useful to identify a) positions in biological sequences that appear to be evolutionarily conserved, and b) positions in biological sequences that appear to interact with one another. In addition, the invention is useful to identify c) the functions of the pathways between interacting positions, and d) the mechanisms responsible for those pathways, or connections. The invention may be used for any biological sequence, including proteins, ribonucleic acids (RNA), deoxyribonucleic acids (DNA), lipids, and polysaccharides (sugars), to name but a few examples. The invention is believed to be particularly useful in the analysis of protein sequences.

The present methods are preferably performed by a suitably programmed machine. For illustration, the following description and examples involve the use of protein/amino acid sequences, but those skilled in the art having the benefit of this disclosure will recognize that the same approach may be used for other biological sequences, as described in greater detail near the end of this disclosure.

A set of amino acid sequences that are members of a common structural family is provided; those amino acid sequences are aligned to produce a multiple sequence alignment (MSA). For each position i in the multiple sequence alignment, a conservation energy value ($\Delta G^{stat}$) is calculated.

The respective conservation energy values represent the overall deviation of amino acid frequencies, at the respective positions, from the mean values (i.e., the expected values) for the amino acids in question. A list of positions with statistically significant conservation energy values is generated. The conservation energy values may be displayed in a graphical image (e.g., a bar graph or a three dimensional map) to aid analysis.

To determine interacting positions, a specific position within the multiple sequence alignment that has a statistically significant conservation energy value is selected. A subset of the full set of amino acid sequences is selected. The subset is analyzed and the vector difference between $\Delta G^{stat}$ of the subset and the $\Delta G^{stat}$ obtained from the larger full set of sequences is calculated. This vector difference ($\Delta\Delta G_{i,j}^{stat}$) represents the degree to which the probability of individual amino acids at position i is dependent on the perturbation at position j. This difference value may be displayed in a graphical image (e.g. a bar graph or a three dimensional map) to aid analysis.

In one respect, the invention is a method of identifying one or more positions in a polymer family. The method includes accessing data representing a multiple sequence alignment (MSA) of a plurality of polymer sequences. The method also includes identifying one or more positions within the MSA that have statistically significant conservation energy values using the following equation:

$$\Delta G_i^{stat} = kT^* \sqrt{\sum_x \left(\ln \frac{P_i^x}{P_{MSA}^x}\right)^2}$$

wherein:
   i is a position in the MSA;
   $\Delta G_i^{stat}$ is the conservation energy value for position i;
   $P_i^x$ is the probability of monomer x at position i;
   $P_{MSA}^x$ is the probability of monomer x in the MSA; and kT* is an energy unit, where k is Boltzmann's constant.

In other aspects, the method may be executed using a machine. The invention may be a program storage device readable by the machine and encoding instructions executable by the machine for performing the steps described above. The method may include generating a graphical image of the conservation energy values (which is described below in greater detail). The polymer sequences may be protein sequences. Monomer x may be amino acid x. The data accessed may be data from the PDZ domain family. The data accessed may also be data from the p21$^{ras}$ domain family. The data accessed may also be from the hemoglobin domain family.

In another respect, the invention is a method of identifying one or more positions in a polymer family. The method includes accessing data representing a multiple sequence alignment (MSA) of a plurality of polymer sequences. The method also includes calculating a conservation energy value for each position in the MSA using the following equation:

$$\Delta G_i^{stat} = kT^* \sqrt{\sum_x \left( \ln \frac{P_i^x}{P_{MSA}^x} \right)^2}$$

wherein:
  i is a position in the MSA;
  $\Delta G_i^{stat}$ is the conservation energy value for position i;
  $P_i^x$ is the probability of monomer x at position i;
  $P_{MSA}^x$ is the probability of monomer x in the MSA; and
  kT* is an energy unit, where k is Boltzmann's constant.

The method also includes identifying one or more positions within the MSA that have statistically significant conservation energy values.

In other aspects, the method may be executed using a machine. The invention may be a program storage device readable by the machine and encoding instructions executable by the machine for performing the steps described above. The method may include generating a graphical image of the conservation energy values (which is described below in greater detail). The polymer sequences may be protein sequences. Monomer x may be amino acid x. The data accessed may be data from the PDZ domain family. The data accessed may also be data from the p21$^{ras}$ domain family. The data accessed may also be from the hemoglobin domain family.

In another respect, the invention is a machine-executed method of quantitatively identifying one or more amino acid positions in a protein family that are suspected to be evolutionarily conserved. The method includes accessing data representing a multiple sequence alignment (MSA) of a plurality of protein sequences that are members of a common structural family. The method also includes for each position in the MSA, calculating a respective conservation energy value using the following equation:

$$\Delta G_i^{stat} = kT^* \sqrt{\sum_x \left( \ln \frac{P_i^x}{P_{MSA}^x} \right)^2}$$

wherein:
  i is a position in the MSA;
  $\Delta G_i^{stat}$ is the conservation energy value for position i;
  $P_i^x$ is the probability of amino acid x at position i;
  $P_{MSA}^x$ is the probability of amino acid x in the MSA; and
  kT* is an energy unit, where k is Boltzmann's constant; and The method also includes identifying one or more positions within the MSA that have statistically significant conservation energy values.

In another respect, the invention is a method useful in identifying interacting monomers in a polymer family. The method includes accessing data representing a multiple sequence alignment (MSA) of a plurality of polymer sequences. The method also includes calculating a respective conservation energy value for each position in the MSA using the following equation:

$$\Delta G_i^{stat} = kT^* \sqrt{\sum_x \left( \ln \frac{P_i^x}{P_{MSA}^x} \right)^2}$$

wherein:
  i is a position in the MSA;
  $\Delta G_{stat}$ is the conservation energy value for position i;
  $P_i^x$ is the probability of monomer x at position i;
  $P_{MSA}^x$ is the probability of monomer x in the MSA; and
  kT* is an energy unit, where k is Boltzmann's constant.

The method includes perturbing a position in the MSA other than position i; re-calculating the respective conservation energy value for each position in the MSA to yield a perturbed conservation energy value; and identifying positions within the MSA that have statistically significant differences between their respective conservation energy values and their perturbed conservation energy values.

In other aspects, the perturbing may include selecting a position j in the MSA; and selecting a subset of the MSA, the subset having one or more monomers at position j in the MSA. The re-calculating and identifying may include for each position in the MSA, calculating a vector difference $\Delta\Delta G^{stat}$ between the conservation energy value of the MSA and a conservation energy value of the subset of the MSA using the following equation:

$$\Delta\Delta G_{i,j}^{stat} = kT^* \sqrt{\sum_x \left( \ln \frac{P_{i|\delta j}^x}{P_{MSA|\delta j}^x} - \ln \frac{P_i^x}{P_{MSA}^x} \right)^2}$$

wherein:
  $\Delta\Delta G_{i,j}^{stat}$ is the vector difference in conservation energy values for position i;
  $P_{i|\delta j}^x$ the probability of monomer x at position i of the subset; and
  $P_{MSA|\delta j}$ is the probability of monomer x in the subset.

The method may also include identifying positions within the MSA that have statistically significant $\Delta\Delta G^{stat}$ values.

In still other aspects, the method may include generating a graphical image of the $\Delta\Delta G^{stat}$ values. The method may be executed using a machine. The invention may be a program storage device readable by the machine and encoding instructions executable by the machine for performing the steps of accessing, calculating, perturbing, re-calculating, and identify recited above. The polymer sequences may be protein sequences. Monomer x may be amino acid x. The data accessed may be data from the PDZ domain family. The data accessed may be data from the $p_{21}{}^{ras}$ domain family. The data accessed may be data from the hemoglobin domain family.

In another respect, the invention is a machine-executed method of quantitatively identifying interacting amino acids in a protein family. The method includes accessing data representing a multiple sequence alignment (MSA) of a plurality of protein sequences that are members of a common structural family. The method also includes for each position in the MSA, calculating a respective conservation energy value using the following equation:

$$\Delta G_i^{stat} = kT^* \sqrt{\sum_x \left( \ln \frac{P_i^x}{P_{MSA}^x} \right)^2}$$

wherein:
  i is a position in the MSA;
  $\Delta G_i^{stat}$ is the conservation energy value for position i;
  $P_i^x$ is the probability of amino acid x at position i;
  $P_{MSA}^x$ is the probability of amino acid x in the MSA; and
  kT* is an energy unit, where k is Boltzmann's constant.

The method includes selecting a position j in the MSA; selecting a subset of the MSA, wherein the subset has one or more amino acids at position j in the multiple sequence alignment; for each position in the multiple sequence alignment, calculating a vector difference between the respective conservation energy value of the multiple sequence alignment and the respective conservation energy value of the subset of the multiple sequence alignment; and identifying positions within the MSA that have statistically significant vector differences.

In another respect, the invention is a method of analyzing data that includes providing at least one protein having a crystal structure and multiple positions; solving the crystal structure of the at least one protein; and identifying pathways between interacting positions on the at least one protein.

In another respect, the invention is a method of analyzing the effect of perturbation on a protein that includes accessing data representing at least one protein and at least one perturbed protein. Both proteins have at least one atom that is identical, or the same. The method also includes calculating a quantity of change $\Delta_{struct}$ to the atom using the following equation:

$$\Delta_{struct} = \frac{|\vec{r}_{mut}|}{\sqrt{\sigma_{mut}^2 + \sigma_{wt}^2}}$$

wherein:
  $|\vec{r}_{mut}|$ is the magnitude of a vector connecting the position of the atom in the at least one perturbed protein and the position of the atom in the at least one protein;
  $\sigma_{mut}$ is a standard deviation of the atom in the at least one perturbed protein; and
  $\sigma_{wt}$ is a standard deviation of the atom in the at least one protein.

In another respect, the invention is a method of analyzing data that includes accessing data representing at least one protein, a first perturbation of the at least one protein yielding a first perturbed protein, a second perturbation of the at least one protein yielding a second perturbed protein, and a double perturbation of the at least one protein yielding a double perturbed protein, the double perturbation comprising both the first and second perturbations. The proteins each have at least one identical atom. The method also includes calculating a quantity of structural coupling $\Delta\Delta_{struct}$ between the first and second perturbations using the following equation:

$$\Delta\Delta_{struct} = \frac{|\vec{r}_{mut1} - \vec{r}_{mut1|mut2}|}{\sqrt{\sigma_{wt}^2 + \sigma_{mut1}^2 + \sigma_{mut2}^2 + \sigma_{mut1,mut2}^2}}$$

wherein:
  $|\vec{r}_{mut1}|$ is a vector connecting the position of the atom in the first perturbed protein and the position of the atom in the at least one protein;
  $\vec{r}_{mt1|mut2}$ is a vector connecting the position of the atom in the double perturbed protein and the position of the atom in the second perturbed protein;
  $\sigma_{wt}$ is a standard deviation of the atom in the at least one protein;
  $\sigma_{mut1}$ is a standard deviation of the atom in the first perturbed protein;
  $\sigma_{mut2}$ is a standard deviation of the atom in the second perturbed protein; and
  $\sigma_{mut1,mut2}$ is a standard deviation of the atom in the double perturbed protein.

In another respect, the invention is a method of analyzing microarray data that includes accessing microarray data representing an expression level of at least one gene, an expression level of the at least one gene resulting from a first perturbation, an expression level of the at least one gene resulting from a second perturbation, and an expression level of the at least one gene resulting from a double perturbation comprising both the first and second perturbations. The method also includes calculating a degree of coupling $\Delta\Delta E$ between the first and second perturbations using the following equation:

$$\Delta\Delta E = kT^* \ln\left(\frac{f_1}{f_2}\right)$$

wherein:
  $f_1$ is the fold effect of the gene due to the first perturbation relative to the at least one gene;
  $f_2$ is the fold effect of the gene due to the double perturbation relative to the second perturbation; and
  kT* is an energy unit, where k is Boltzmann's constant.

BRIEF DESCRIPTION OF THE DRAWINGS

The following figures form part of the present specification and are included to further demonstrate certain aspects of the present invention. The invention may be better understood by reference to one or more of these drawings in combination with the detailed description of specific embodiments presented herein.

| FIG. | Description |
|---|---|
| 1 | Histograms of amino acids for all 36,498 entries in the Swiss-Prot database (as of 10/98) and for 274 members of the PDZ protein family. Black bars represent all Swiss-Prot proteins, gray bars represent the PDZ protein family. |
| 2 | Histogram of amino acids at position 76 of PDZ multiple sequence alignment. Black bars represent all Swiss-Prot proteins, gray bars represent position 76. Position 76 is highly conserved, as evidenced by the high distribution values (Y-axis). |
| 3 | Histogram of amino acids at position 99 of PDZ multiple sequence alignment. Black bars represent all Swiss-Prot proteins, gray bars represent position 99. Position 99 is weakly conserved, as evidenced by the low distribution values (Y-axis). |
| 4 | Calculated $\Delta G^{stat}$ for all positions in PDZ multiple sequence alignment. The statistical energy ($\Delta G^{stat}$) representing evolutionary conservation is plotted against the primary structure position. |
| 5 | Thermodynamic cycle describing statistical coupling. |
| 6 | Thermodynamic cycle describing mutational coupling. |
| 7 | Amino acid distributions at positions 67 and 34 before (black bars) and after (gray bars) a 6.45 kT* perturbation at position 76. Note that the distribution at position 67 changes very little upon perturbation at position 76 despite high overall conservation, and that the distribution at position 34 changes significantly. |
| 8 | A full mapping of $\Delta\Delta G_{i,j}^{stat}$ for PDZ position 76 for all other positions in the fold family. Only a small set of coupled positions distributed throughout the primary sequence emerge above noise. |
| 9 | Statistical coupling ($\Delta\Delta G^{stat}$) with sites categorized in three groups: sites that are statistically coupled and near to position 76 [33,34,39,80,84], sites that are statistically coupled but distant from position 76 [26,29,66,67,90], and sites that are statistically uncoupled [32,44,75,89]. |
| 10 | Mutational coupling ($\Delta\Delta G^{mut}$), with sites categorized in three groups: sites that are statistically coupled and near to position 76 [33,34,39,80,84], sites that are statistically coupled but distant from position 76 [26,29,66,67,90], and sites that are statistically uncoupled [32,44,75,89]. Inset is a binding isotherm for wild-type PDZ3$^{psd95}$ protein and a class I binding peptide. An average and standard deviation of five measurements are shown for each ligand concentration tested, with the smooth curve showing a fit to the Hill equation. |
| 11 | Scatter plot of mutational coupling energies and statistical coupling energies. This plot demonstrates good prediction of thermodynamic coupling through the statistical analysis. |
| 12 | Thermodynamic mutant cycle analysis between mutations at PDZ position 76 (H76Y) and mutations at ligand positions at the directly-interacting position (T7F) and at the carboxyl-terminal position (V9A). This suggests coupling of both peptide positions with PDZ position 76. |

DEFINITIONS

Figure 1:
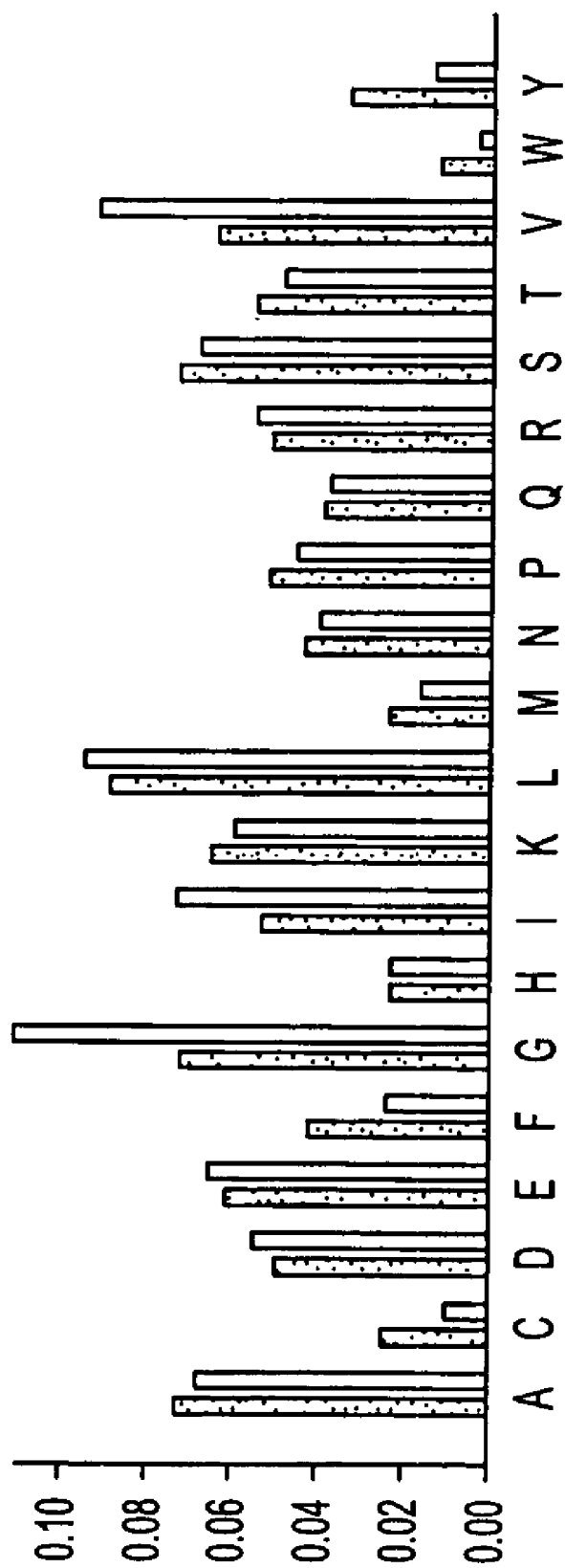

The following definitions are provided in order to aid those skilled in the art in understanding the detailed description of the present invention.

"Evolutionarily conserved amino acid positions" refers to particular positions within a multiple sequence alignment which display a non-zero $\Delta G^{stat}$ as calculated by Equation 4. In general terms, this refers to positions within a sequence that have a non-random distribution of monomers. For example, if many members of a protein family have histidine at position 50, this would suggest that having histidine at position 50 is important for the protein's function, and that it has been conserved during evolution. Conversely, if position 50 in the members of the protein family displayed a random distribution of amino acids, this would suggest that there was no requirement for any particular amino acids at this position during evolution.

"Multiple sequence alignment" (MSA) refers to an optimized alignment of two or more sequences. Protein multiple sequence alignments may be performed manually or by computer programs, e.g. CLUSTALW (Thompson, et al. *Nucl. Acids Res.*, 22: 4673–4680, 1994). Multiple sequence alignments performed by computer programs may be subsequently modified manually if more detailed structural information is known about the protein sequence or structure.

"Protein sequence" and "amino acid sequence" refer to the amino acid sequence that constitutes a protein. Amino acids are commonly referred to by their one letter abbreviations: Alanine, A; Cysteine, C; Aspartic acid, D; Glutamic acid, E; Phenylalanine, F; Glycine, G; Histidine, H; Isoleucine, I; Lysine, K; Leucine, L; Methionine, M; Asparagine, N; Proline, P; Glutamine, Q; Arginine, R; Serine, S; Threonine, T; Valine, V; Tryptophan, W; Tyrosine, Y.

"Protein family" or "structural family" refers to a set of protein sequences that may be aligned. The protein family may have the same biological or enzymatic function, (e.g., a set of DNA polymerases or glutamate dehydrogenases), or a common structural region (e.g., a set of proteins containing a zinc finger region).

"Statistically significant conservation energy values" may vary with the application. In general, this refers to values that are greater than the background "noise" value. One manner of arriving at values that are greater than the background noise is to fit the set of energy values for all positions in an alignment to well-established Gaussian error models. Values greater than two standard deviations from the mean may be classified as "statistically significant."

DESCRIPTION OF ILLUSTRATIVE EMBODIMENTS

The illustrative method described below incorporates the essential features of the evolutionary process in two guiding principles: (1) positions on the protein that are not constrained by the energetic requirements of folding or function should show an amino-acid distribution that approaches the mean overall amino-acid distributions found in all natural proteins; and (2) the conserved functional interaction of two positions in any protein family should make the amino-acid distributions dependent on each other; thus, the outcome at one position should influence the outcome at the other coupled position. A corollary of (1) is that conservation at any given position can be quantitatively regarded as the degree to which the amino-acid distribution at that position deviates from the mean distribution in all proteins. The folding of a protein is the process by which the linear amino-acid sequence of a protein generates the three-dimensional structure of the protein.

A first step is the calculation of conservation at each position in a multiple sequence alignment. Each position on the sequence alignment may be characterized by a vector of amino-acid frequencies:

$$f_i = (f_{ala}, f_{cys}, \ldots, f_{tyr}) \qquad \text{(Equation 1)}$$

In the limit where an infinity of observed sequences is available for analysis, this vector should just be the probabilities of each amino acid at position i. Since one normally has only several hundred sequences of each protein family at best, the probabilities given these observed frequencies are estimated using probability theory. The binomial distribution gives the probability of n observations of amino acid x out of a total of N sequences when the mean probability of amino acid x is $p_x$:

$$P_i^x = \frac{N!}{n_x!(N-n_x)!} p_x^{n_x}(1-p_x)^{N-n_x} \quad \text{(Equation 2)}$$

Thus the frequency vector may be converted to a probability vector for site i by using this equation for each element of the vector of amino acid frequencies.

In order to investigate the energetic interactions of sites on a protein, it is preferable for the statistical parameters to also have energy-like characteristics. This greatly simplifies the interpretation of the data, especially in drawing the conceptual analogy of this method to mutagenesis in proteins. The Boltzmann distribution of classical thermodynamics gives the relationship of the relative probability of two states (i and j) of a system to the statistical energy ($\Delta G_{i \to j}^x$) separating these states:

$$\frac{P_i^x}{P_j^x} = e^{-\frac{\Delta G_{i \to j}^x}{kT^*}} \quad \text{(Equation 3)}$$

Using this equation, the probability vector is converted to a vector of statistical energies where each element is now the statistical energy representing the deviance of each amino acid from the mean value expected for all proteins. The magnitude of this vector is the empirical parameter (in energetic units, $kT^*$) that quantitatively represents conservation at any given site i of a sequence alignment:

$$\Delta G_i^{stat} = kT^* \sqrt{\sum_x \left(\ln \frac{P_i^x}{P_{MSA}^x}\right)^2} \quad \text{(Equation 4)}$$

This analysis may be used, for example, to identify the active site (the functional surface), binding site, or allosteric site of a protein.

An additional embodiment of the invention is the subsequent energetic measurement of coupling of two positions on a protein. This amounts to determining whether the amino acid frequencies at one site are affected by changes at another site. To address this, a change is made to the observed amino acid frequencies at one site j by selecting out a subset of the sequence alignment. This selecting out causes a change in the frequencies at site j. For example, if a position started with 0.6H and 0.4V, selecting out all sequences that have only H at that site would have the effect of changing the frequencies at that site to 1.0H. After making such a selection, the vector of statistical energies is then re-calculated at each position i of the subset alignment. The difference in the statistical energy vector at a site i before and after the change at j is a measure of the interdependency of the two sites. This is intuitive in that if site i were totally independent of j, then any change made at j is very unlikely to result in any change at i. The coupling between sites i and j is calculated as the magnitude of the difference vector at i before and after the perturbation at site j.

$$\Delta\Delta G_{i,j}^{stat} = kT^* \sqrt{\sum_x \left(\ln \frac{P_{i|\delta j}^x}{P_{MSA|\delta j}^x} - \ln \frac{P_i^x}{P_{MSA}^x}\right)^2} \quad \text{(Equation 5)}$$

Mean Distribution of Amino Acids

In nature, the twenty naturally occurring amino acids are not used equally. The mean distributions of amino acids may be obtained from scientific publications, the internet, or may be generated from a suitable database such as PIR, GenBank, or SwissPROT. In order to generate mean distributions, a collection of proteins is selected, and the occurrence of each amino acid is calculated as a decimal fraction of the total number of amino acid residues in the collection. For example, if a selected collection of 300 protein sequences containing a total of 300,000 amino acid residues has 21,477 glycines, the mean frequency of glycine would be calculated to be 0.07159 (21477/300000).

Multiple Sequence Alignments

Protein sequences may be aligned to optimize the alignment of identical or similar amino acids, affording a "multiple sequence alignment" representing similar three dimensional structures. Multiple sequence alignments may be performed manually, or preferably by a computer program such as CLUSTALW or other commercial or publicly-available programs.

Statistical Analysis of Conservation

For an evolutionarily well-sampled multiple sequence alignment, where adding additional sequences does not change the distribution at sites much, the probability of any amino acid x at site i relative to the probability of the amino acid at another site, j, is related to the statistical free energy separating i and j for the $x^{th}$ amino acid ($\Delta G_{i \to j}^x$) by the Boltzmann distribution computed in accordance with Equation 3 (Tolman, R. C. *The Principles of Statistical Mechanics* (Dover Publications Inc., New York, 1938), where $kT^*$ is an arbitrary energy unit. For conventional statistical mechanical systems at equilibrium, the temperature (T) of an ensemble is proportional to the mean velocity of state transitions, and defines the fundamental energy unit kT, where k is Boltzmann's constant. In our analysis, we treat sites on a multiple sequence alignment as individual statistical mechanical systems that can be represented as discrete states in an overall state space of amino-acid frequencies. The "temperature" ($T^*$) of an ensemble of such systems is again related to the mean transition rates between states, but we note that the energy unit in such a system ($kT^*$) is not necessarily related to that for conventional mechanical systems.

The probability of any amino acid x at site i ($P_i^x$) is given by the binomial probability of the observed number of $x^{th}$ amino acids given its mean frequency in all proteins. The full distribution of amino acids at a site can then be characterized by a twenty-element vector of $P_i^x$ for all x ($\overline{P_i^x}$) Looking at a hypothetical site where all amino acids are found at their mean frequencies in the MSA as a reference state for all sites, Equation 3 may be used to transform $\overline{P_i^x}$ into a vector of statistical energies which represents the evolutionary constraint at site i. An overall empirical evolutionary conservation parameter ($\Delta G^{stat}$) is defined for site i per Equation 4.

For each position in the generated multiple sequence alignment, $\Delta G^{stat}$ is calculated using Equation 4. A list of positions within the multiple sequence alignment having statistically significant conservation energy values is generated. That is, one may identify the position or positions within the MSA that have statistically significant conservation energy values. As explained above, this may be achieved by fitting the set of energy values for all positions in the MSA to well-established Gaussian error models. Values greater than two standard deviations from the mean may be classified as statistically significant. Optionally, a graphical display of the conservation energy values may be generated using commercial or publicly available graphing software.

Statistical Analysis of Coupling

Functional coupling of sites should mutually constrain the evolution of those sites, and therefore their amino acid distributions in a sequence alignment should be statistically correlated. To measure this, the conservation energy value at a given site i is measured under two conditions: (1) the full set multiple sequence alignment, and (2) a selected subset of the multiple sequence alignment representing a perturbation of the amino acid frequencies at another site j. The magnitude of the difference in these two energy values ($\Delta\Delta G_{i,j}^{stat}$) quantitatively represents the degree to which the probability of individual amino acids at position i is dependent on the perturbation at position j (see Equation 5).

The multinomial probability for all 20 amino acids provides the overall probability of observing a given amino acid distribution at a site, but is degenerate given redistribution of amino acids with similar mean frequency. This suggests that even significant changes in the amino acid composition at one site upon perturbation at another may go unrecognized if measured as changes in this value. For example, consider a site that displays a distribution 0.4 Ala, 0.4 Asp, 0.2 Ile in the overall alignment, and which changes to 0.4 Ala, 0.2 Asp, 0.4 Ile upon perturbation at another site. Since the mean frequency of Asp and Ile is nearly identical (FIG. 1), the multinomial probability of these two distributions are the same though the significant reorganization of chemical character suggests that these positions are indeed coupled. The inventive method described accounts for all such cases by treating sites as vectors of individual amino acid probabilities, where each amino acid distribution maps to a unique vector.

The following Examples are included to demonstrate preferred embodiments of the invention. It should be appreciated by those of skill in the art that the techniques disclosed in the Examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Computations Using Software

Software implementing the approach described above was written in C for DEC alpha platforms running DEC Unix. A copy of the source code is reproduced in the Appendix. For calculation of the mean frequencies of amino acids, we selected all eukaryotic sequences from the Swiss-Prot database (as of October 1998) parsed for truncation of the pre/pro sequences, and made histograms (i.e., graphs) of amino-acid frequencies. Statistical energies at positions in a multiple sequence alignment are calculated as follows. Each position in a multiple sequence alignment can be described as a twenty-element vector of individual amino acid frequencies. Each element is transformed into a probability for that amino acid using the binomial density function:

$$P(x) = \frac{N!}{x!(N-x)!} p^x (1-p)^{N-x} \qquad \text{(Equation 6)}$$

where N is the total number of sequences, x is the number of sequences with a given amino acid, and p is the mean frequency of that amino acid in all proteins.

Each element in the probability vector is then converted to a statistical energy for that amino acid using Equation 4, where a hypothetical site where the amino acids are found at their mean frequency in the multiple sequence alignment is taken as the reference state. The scalar statistical energy of conservation for a site ($\Delta G_i^{stat}$) is given by the magnitude of the statistical energy vector. Equation 4 summarizes the conversion of amino acid probabilities to $\Delta G_i^{stat}$. Stirling's approximation was used for evaluation of large factorials (>170). For visualization and analysis, statistical energies were arbitrarily scaled by 0.01 for compatibility with GRASP, and outputted in Excel (Microsoft) format or written to a protein data bank (PDB) file of a representative member of the fold family. A fold family is a group of proteins that share an overall three-dimensional structure. Mapping of statistical energies onto tertiary structures was done using GRASP (Nicholls, A. et al., *Proteins* 11: 281, 1999). As used herein, "tertiary structures" are essentially synonymous with three-dimensional structures for single protein chains.

Example 2

Laboratory Methods

Fluorescence energy transfer experiments were carried out using a luminescence spectrometer (Perkin Elmer LS 50 B). A final concentration of 100 nM EGFP-PDZ fusion protein in storage buffer was used for peptide titrations. EGFP was excited at 475 nm and emission was measured at 508 nm. Ligand peptides were synthesized with an N-terminal tetramethylrhodamine adduct, and were freshly diluted from a single batch of 6 μM frozen aliquots for binding measurements. For all measurements, we used the following binding peptide (or mutants thereof, as indicated) co-crystallized in the original structure determination. Energy transfer was followed by quenching of fluorescence at 508 nm, corrected for peptide fluorescence. Transfer efficiencies measured for four or five peptide concentrations covering a two log-order range around the $K_d$ were used for each binding energy calculation; each individual measurement was made 3 to 5 times. Data were fit to the Hill equation (Origin, MicroCal Software, Northampton, Mass.).

Site-directed mutagenesis on the rat PSD-95 third PDZ domain (residues 294–402) was carried out using standard PCR-based techniques (Sambrook, J. et al. Molecular Cloning: A Laboratory Manual, $2^{nd}$ Ed., Cold Spring Harbor, N.Y., 1989). Domains were expressed as C-terminal fusions with the enhanced green fluorescent protein (EGFP, Heim, R. and Tsien, R. Y., *Curr. Biol.* 6: 178–181, 1996) using the pRSET-R vector (Invitrogen, Carlsbad, Calif.) in *E. coli* (BL21(DE3), Stratagene, La Jolla, Calif.). In each case, 500 mL cultures in TB+100 μg/ml ampicillin were grown to an $OD_{600}$ of 1.2 at 37° C., induced for 4 hours with 100 μM IPTG and harvested. Cells were lysed with 20 mL B-PER (Pierce) for 20 minutes at room temperature and centrifuged 20 minutes at 43,000×g at 4° C. Protein was batch-bound to 0.5 mL bed volume of Ni-NTA agarose beads (Qiagen, Valencia, Calif.) prewashed in binding buffer (25 mM Tris (pH 8.0), 500 mM NaCl, 10 mM imidazole) with 0.1% Tween-20, washed with 50 column volumes of binding buffer, and eluted with Elution Buffer (50 mM Tris (pH 8.0), 1 M NaCl, 200 mM imidazole). The protein was dialyzed overnight into storage buffer (50 mM Tris (pH 8.0), 100 mM NaCl, 1 mM DTT) at 4° C. and used immediately for binding assays or flash frozen and stored at −80° C. for later use.

Example 3

Conservation of Amino Acids in PDZ Domains

To determine mean amino-acid frequencies in all proteins, histograms of amino acids for all 36,498 entries in the Swiss-Prot database (as of October 1998) of eukaryotic non-redundant proteins were created, and the mean values were calculated (FIG. 1, black bars). Since all structural and functional information has been scrambled in this analysis, the frequencies of amino acids should represent that which is expected without any functional evolutionary constraint.

The PDZ domain family was selected as one model system for the analyses described below. PDZ domains are a family of small, evolutionarily well-represented protein binding motifs for which four high-resolution structures of distantly related members exist (Doyle, D. A. et al., *Cell* 85: 1067–1076, 1996; Cabral, J. H. et al., *Nature* 382: 649–652, 1996; Daniels, D. L. et al., *Nat. Struct. Biol.* 5: 317–325, 1998; Ranganathan, R., unpublished results). The structures are remarkably similar (RMS deviation in $C_\alpha$ atoms of 1.4 Å) though the average sequence identity between pairs of domains is only 24%, and in many cases is indistinguishable from random. Structure-based alignment techniques were used to generate a multiple sequence alignment of 274 eukaryotic PDZ domains.

Eukaryotic PDZ domains were collected from the non-redundant database using PSI-BLAST (Altschul, S. F. et al., *Nucl. Acids Res.* 25: 3389–3402, 1997); four PDZ domains with known structures (Doyle, D. A. et al., *Cell* 85: 1067–1076, 1996; Cabral, J. H. et al., *Nature* 382: 649–652, 1996; Daniels, D. L. et al., *Nat. Struct. Biol.* 5: 317–325, 1998; Ranganathan, R., unpublished results) were used in initial searches. All non-redundant PDZ domain sequences with an e-score equal to or less than 0.001 were included for alignment. An initial alignment was created using PILEUP (Genetics Computer Group, Madison, Wis.). Blocks of sequences with relatively high internal homology were subjected to structure-based manual alignment (reviewed in Doolittle, R. *Meth. Enzymol.* 266, 1996), and then aligned with homologous blocks. This process was iterated until all blocks were aligned.

Figure 2:
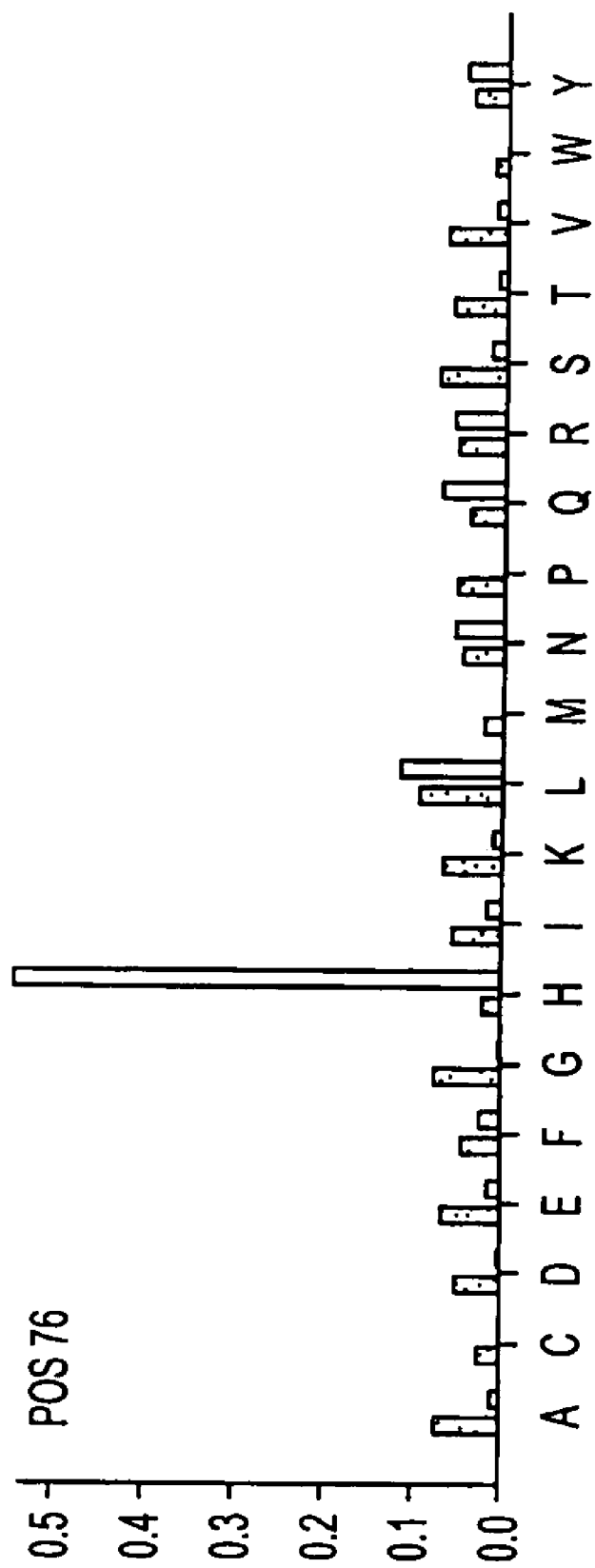
Figure 3:
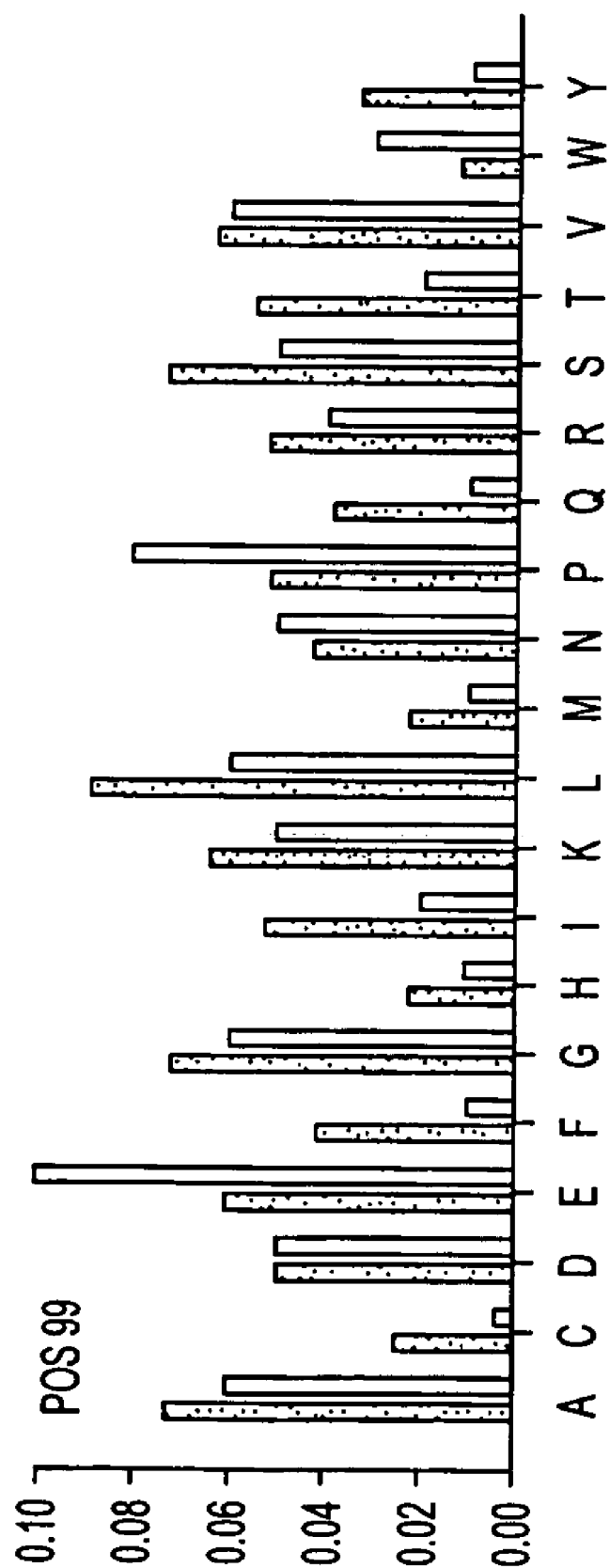

Interestingly, overall amino acid distributions for all proteins (FIG. 1, black bars) and for PDZ domains alone (FIG. 1, gray bars) differ only modestly, a fact that derives from the large sequence divergence of this fold family. Distributions at sites that 9 represent moderately conserved (FIG. 2, Pos 76, $\Delta G^{stat}=3.83$ kT*, σ=0.4 kT*) and weakly-conserved (FIG. 3, Pos 99, $\Delta G^{stat}=0.1$ kT*) positions show that even moderate conservation skews the mean amino acid distribution significantly, and lack of conservation is indeed correlated with distributions closer to the mean.

Figure 4:
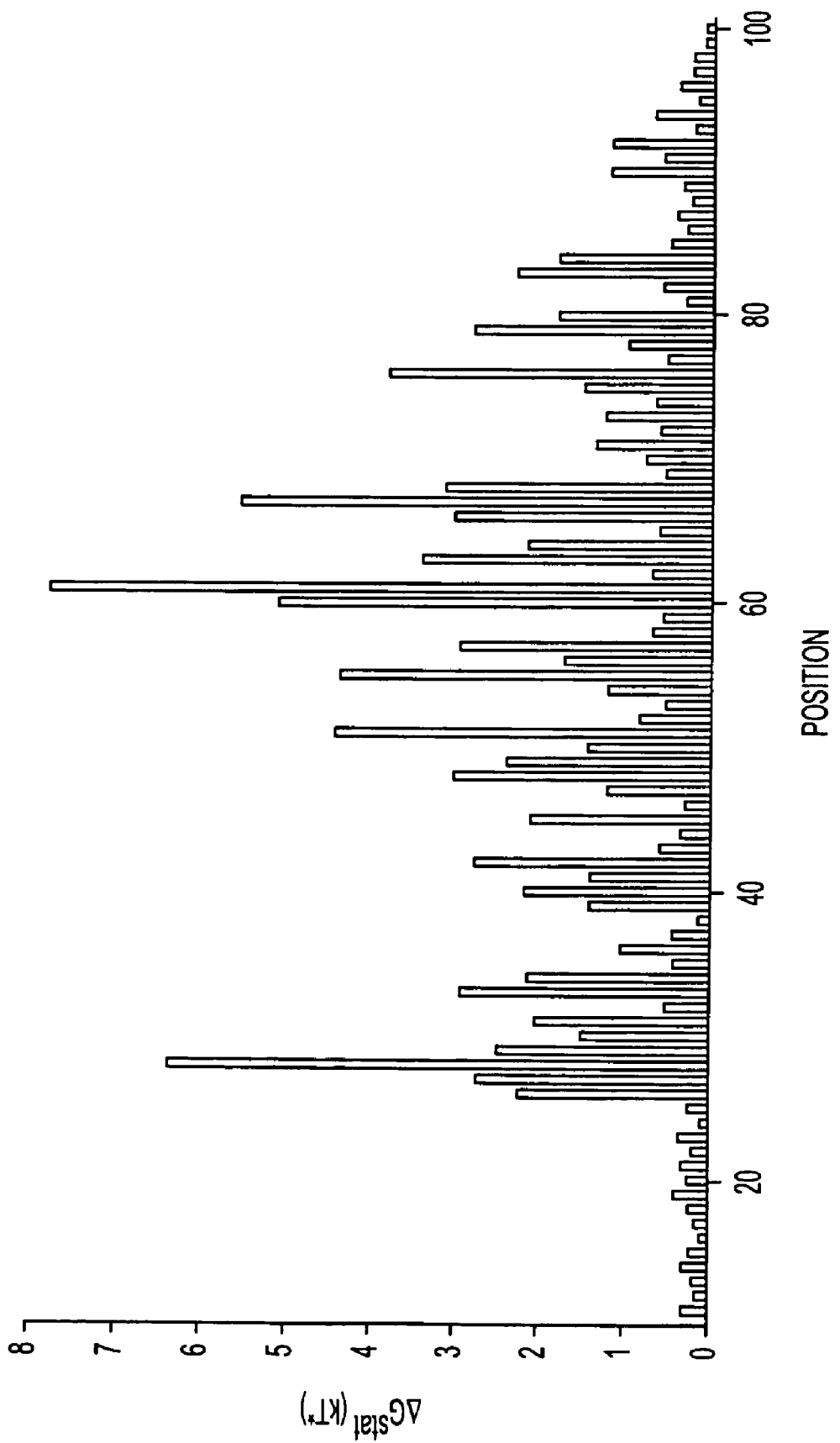

Equation 4 was used to calculate $\Delta G^{stat}$ for all positions on the PDZ domain alignments. These data plotted on the primary structure show a dispersed pattern that describes the overall energetic profile of the fold family (FIG. 4). Not surprisingly, the same data plotted on a representative three-dimensional structure of a member of the family shows that this pattern simplifies into a rough description of the protein interaction surface of the fold (Lichtarge, O. et al., *J. Mol. Biol.* 257: 342–358, 1996). For example, the groove on the surface of the PDZ domain that contains the co-crystallized peptide ligand (Doyle, D. A. et al., *Cell* 85: 1067–1076, 1996; Cabral, J. H. et al., *Nature* 382: 649–652, 1996) emerges as the most conserved portion of the protein family. This finding is consistent with the intuitive expectation that a proper measure of conservation should be able to map functionally important sites on a protein.

Example 4

Coupling of Amino Acids in PDZ Domains

To characterize this energetic coupling function, one functionally important site in the PDZ domain family was selected as a test case for the perturbation analysis. The PDZ domain family is divided into distinct classes based on target sequence specificity; class I domains bind to peptide ligands of the form —S/T—X—V/I—COO⁻ where X represents any amino acid, and class II domains bind to sequences of the form —F/Y—X—V/A—COO⁻ (Songyang, Z. et al., *Science* 275: 73–77, 1997; Ponting, C. P. et al., *Bioessays* 19: 469–479, 1997). An important determinant of ligand specificity is domain position 76 (Doyle, D. A. et al., *Cell* 85: 1067–1076, 1996; the numbering scheme for the PDZ domain used is consistent with that reported for the structures used for mapping statistical energies), which appears to select the identity of the antepenultimate peptide position. In class I domains, a histidine at this position hydrogen bonds to the serine or threonine hydroxyl of the characteristic recognition motif (Doyle, D. A. et al., *Cell* 85: 1067–1076, 1996).

For analysis of statistical coupling, we selected sequences from the multiple sequence alignment representing an alteration to the distribution of amino acids at one site, and recalculated statistical energy vectors at all sites. For example, at PDZ position 76, we extracted the subset of sequences containing histidine at that position as the "perturbed" multiple sequence alignment. The statistical coupling energy for site i given a perturbation at j (δj) is the magnitude of the difference in energy vectors before and after the perturbation (see Equation 5). All distributions were normalized for comparison.

Figure 7:
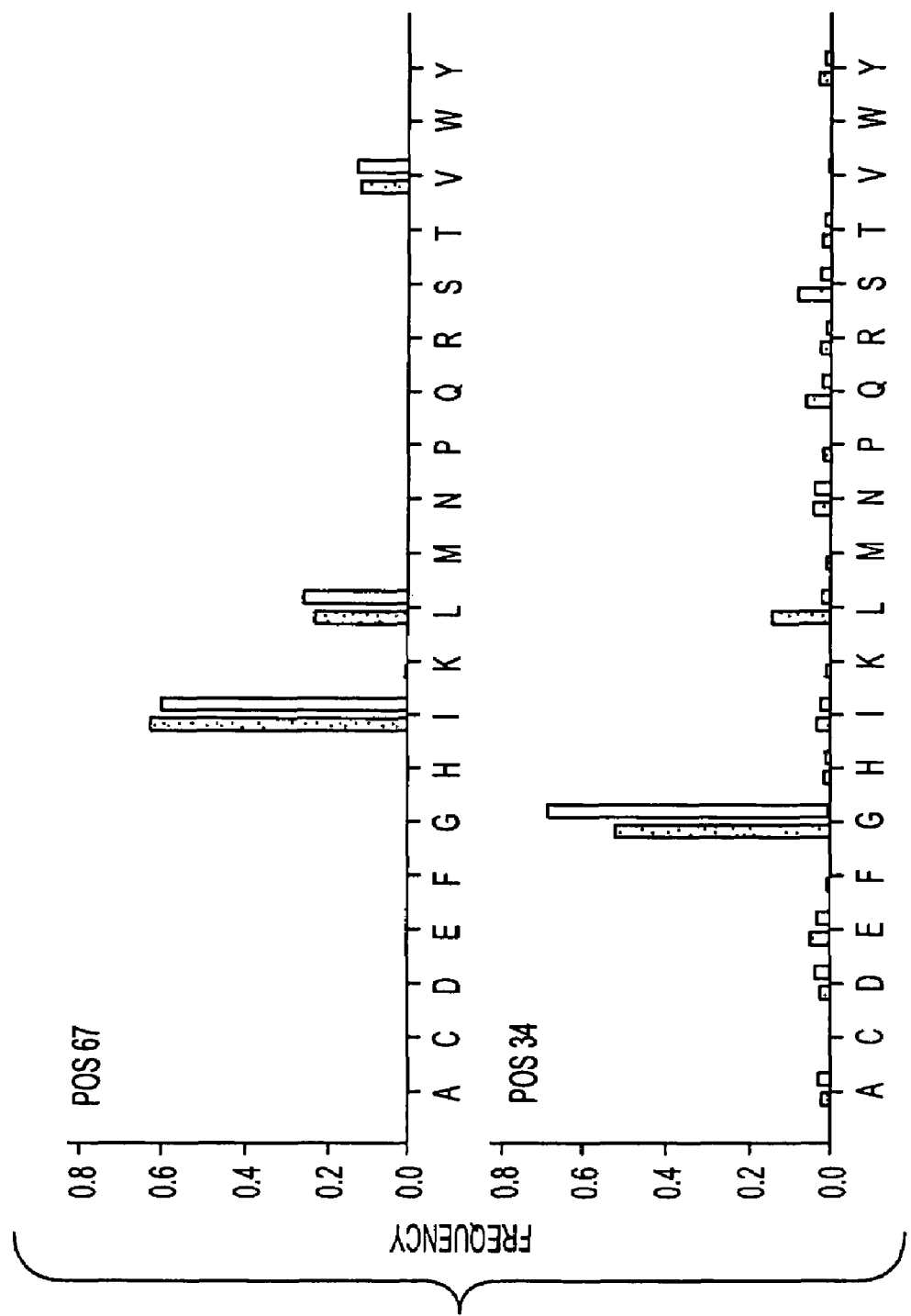

To examine the full pattern of energetic connectivity for PDZ position 76, we made a perturbation to the amino acid distribution at this site by extracting the subset of the multiple sequence alignment that contains only histidine at this position. The statistical energetic consequence of this perturbation is a 6.45 kT* change at position 76 from the full multiple sequence alignment. FIG. 3a shows examples of amino acid distributions for two PDZ positions that illustrate statistical coupling to position 76. Position 63 is highly conserved in all PDZ domains, showing a distribution that is virtually exclusive for leucine, isoleucine, or valine (FIG. 7, upper panel), but one that is largely unaffected by the perturbation at position 76. Consequently, this position displays a low coupling energy ($\Delta\Delta G_{63,76}^{stat}=0.31$ kT*, $\sigma=0.3$ kT*) with respect to position 76. In contrast, the distribution at position 34 changes for several amino acids upon perturbation at position 76 (FIG. 7, lower panel), resulting in significant statistical coupling ($\Delta\Delta G_{80,76}^{stat}=1.32$ kT*).

Figure 8:
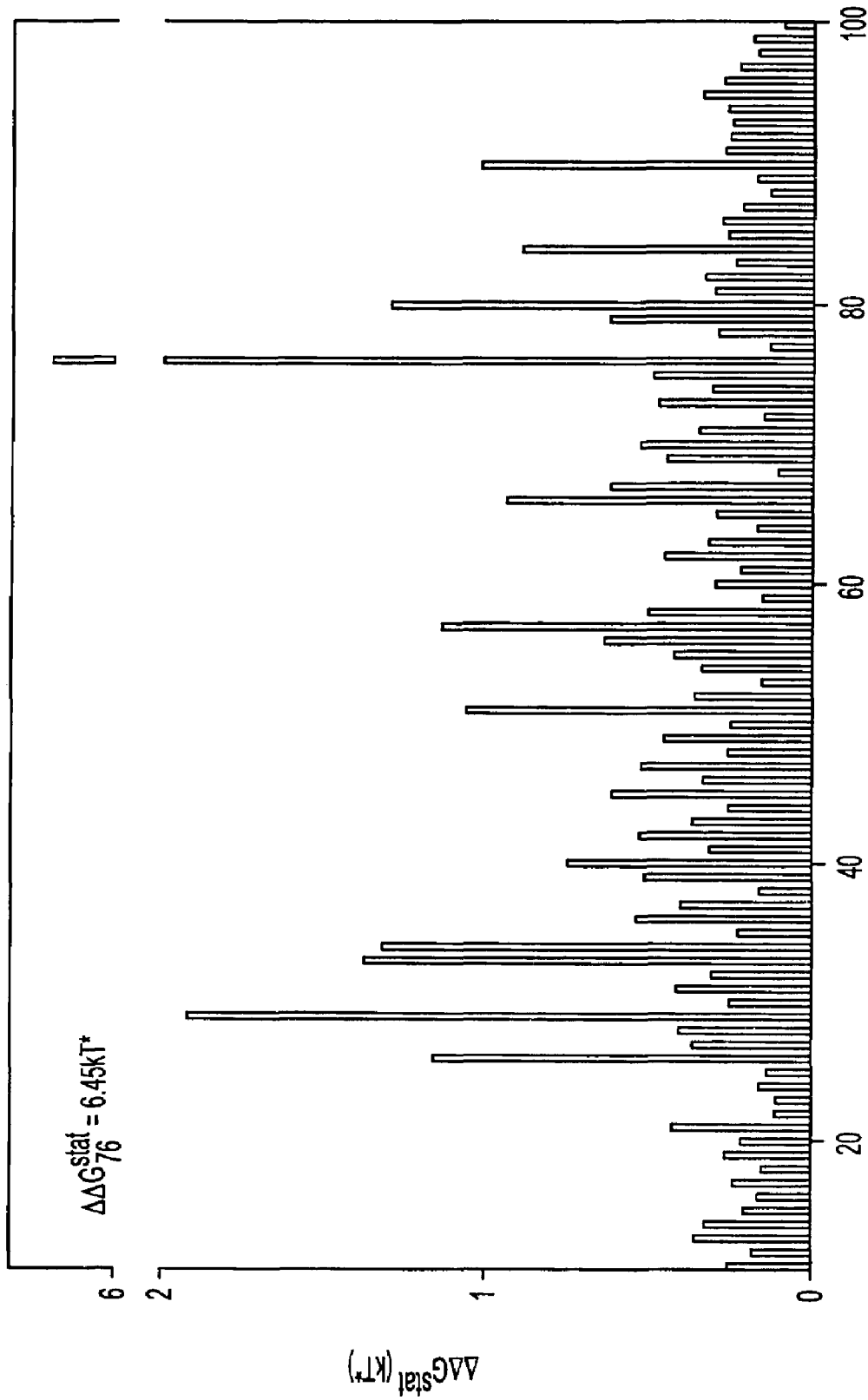

FIG. 8 shows a full primary sequence mapping of statistical coupling for PDZ position 76. Interestingly, these data show that most positions in the fold family are not coupled to the perturbed site; instead, only a small set of statistical couplings emerges from noise. Mapping the data on the PDZ domain tertiary structure shows that the coupled sites fall into three classes. A small set of residues [positions 80, 84, 33, 34] are in the immediate environment of position 76, a finding consistent with expected local propagation of energy from a site of perturbation. In addition, other interaction surface residues implicated in target sequence recognition [positions 29, 26] emerge as coupled. This result suggests energy propagation through bound substrate, and would be an expected consequence of cooperative interaction of binding site residues. Finally, we observe unexpected coupling at long range from sites in the core and on the opposite side of the PDZ domain [positions 51, 57, 66].

Example 5

Mutant Cycle Studies

Figure 5:
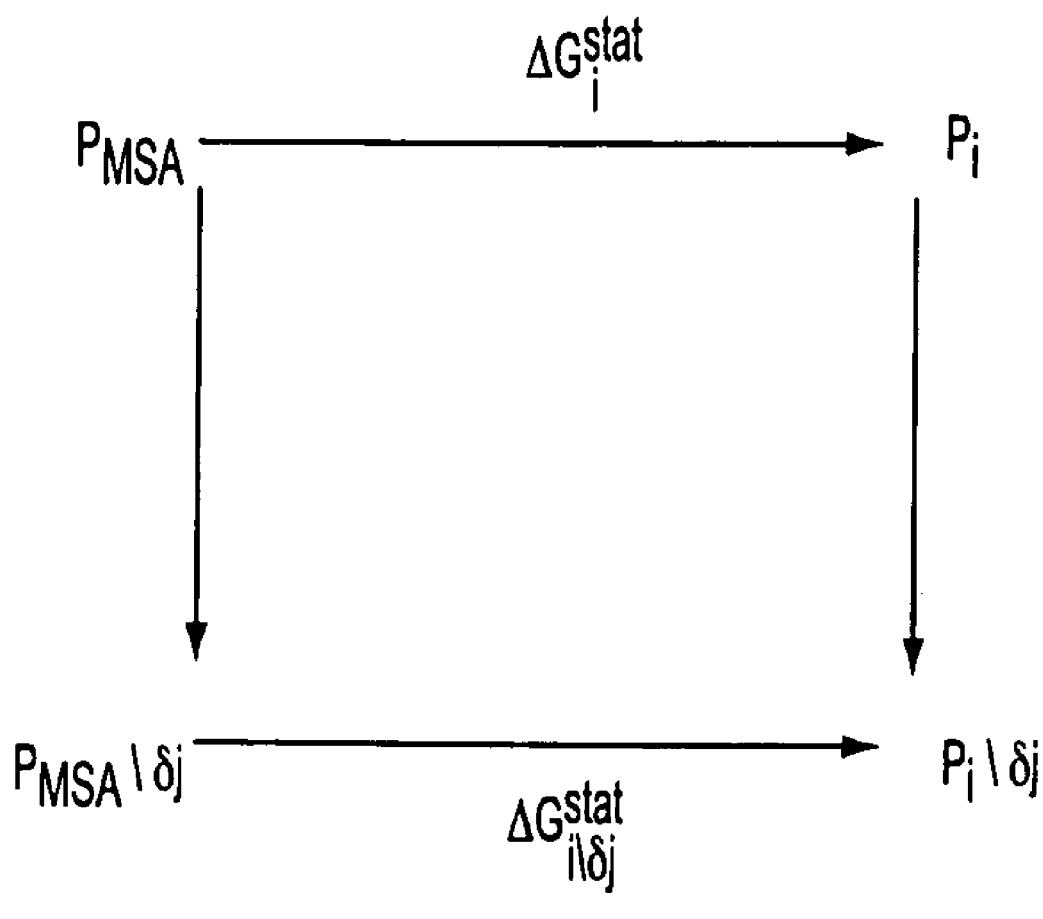
Figure 6:
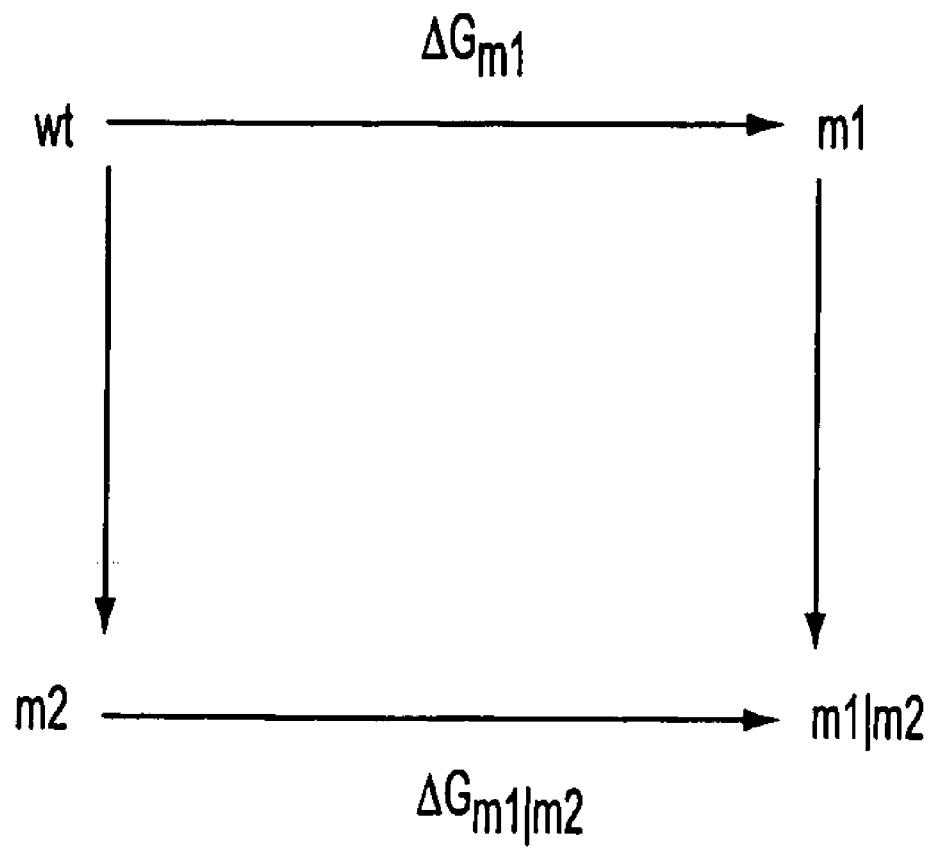

To address the relationship of statistical coupling and the physical energetic coupling of sites, we used the technique of thermodynamic mutant cycle analysis (Hidalgo, P. and MacKinnon, R., *Science* 268: 307–310, 1995; Carter, P. J. et al., *Cell* 38: 835–840, 1984) to measure mutational coupling energies for position 76 for one PDZ domain (PDZ3$^{psd-95}$) and compared these data to the statistical predictions. In the mutant cycle method, the energetic effect of one mutation, m1, is measured for two conditions: (1) the wild-type background ($\Delta G_{m1}$) (FIG. 6) or (2) the background of a second mutation, m2 ($\Delta G_{m1|m2}$) (FIG. 6). This method is analogous to the method of thermodynamic mutant cycle analysis as shown in FIG. 5. The difference in these two energies gives the coupling energy ($\Delta\Delta G_{m1,m2}$) between the two mutations. Note that if m1 does not have the same effect in condition 1 and 2 ($\Delta G_{m1|m2} \neq \Delta G_{m1}$), then $\Delta\Delta G_{m1,m2}$ is non-zero and indicates thermodynamic coupling of the two mutations.

Figure 10:
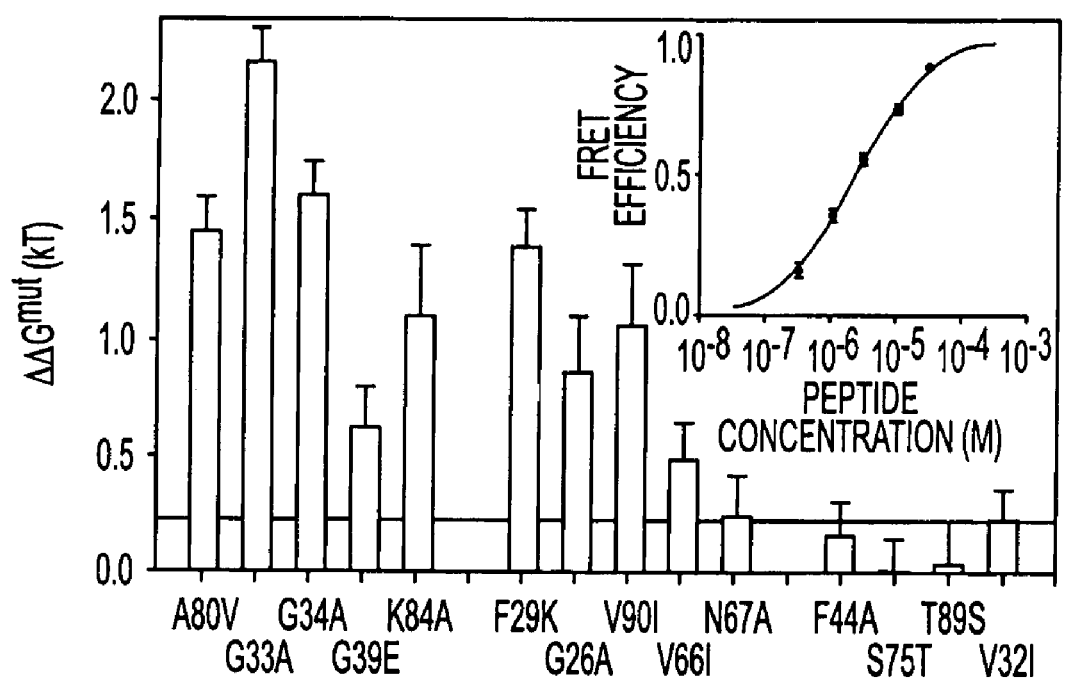

To follow energetic coupling, an equilibrium binding energy assay was developed based on fluorescence resonance energy transfer between green fluorescent protein (GFP)-PDZ domain fusion proteins and tetramethylrhodamine (TMR)-labeled interacting peptides. The inset in FIG. 10 shows a binding isotherm for interaction a wild-type GFP-PDZ3$^{psd-95}$ protein and a TMR-labeled class I peptide, showing that this assay is capable of high-resolution mapping of binding energies.

Figure 9:
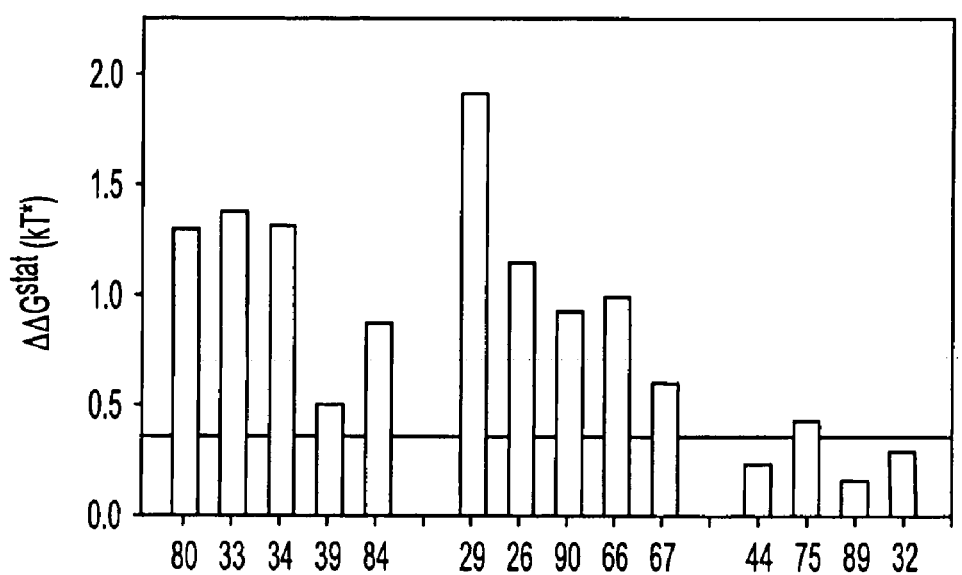
Figure 11:
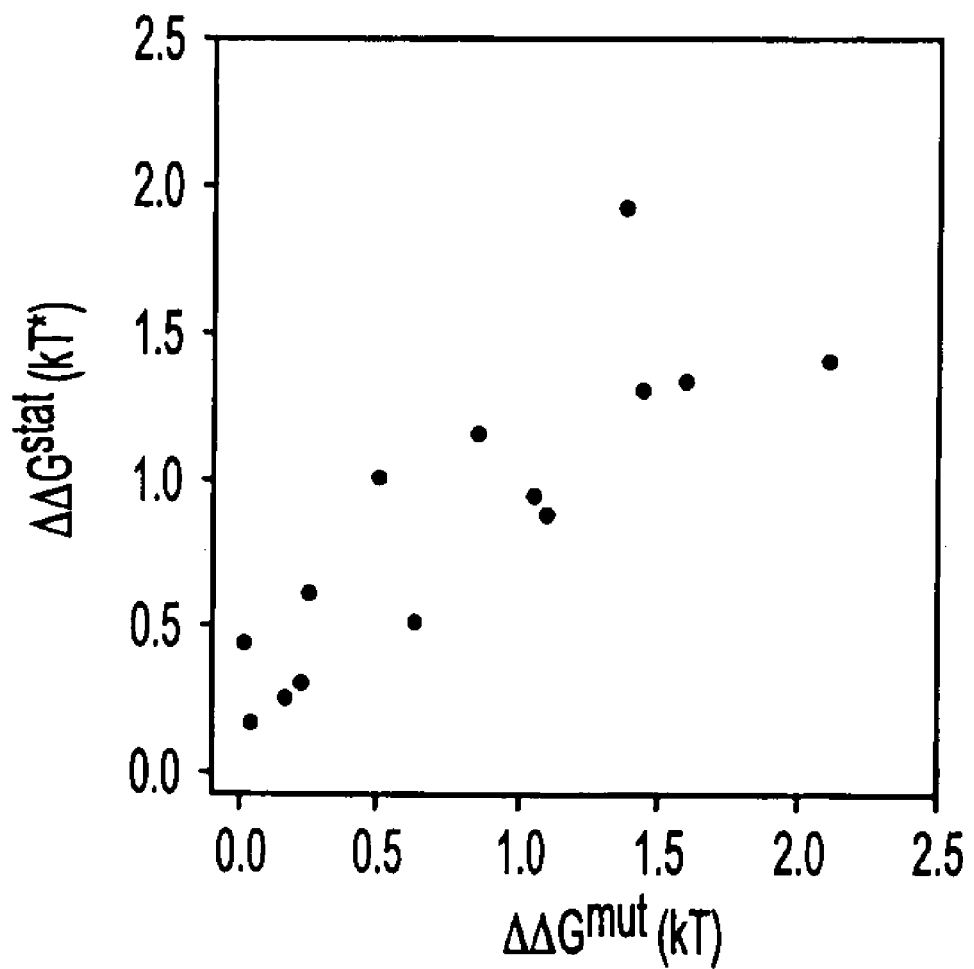
Figure 12:
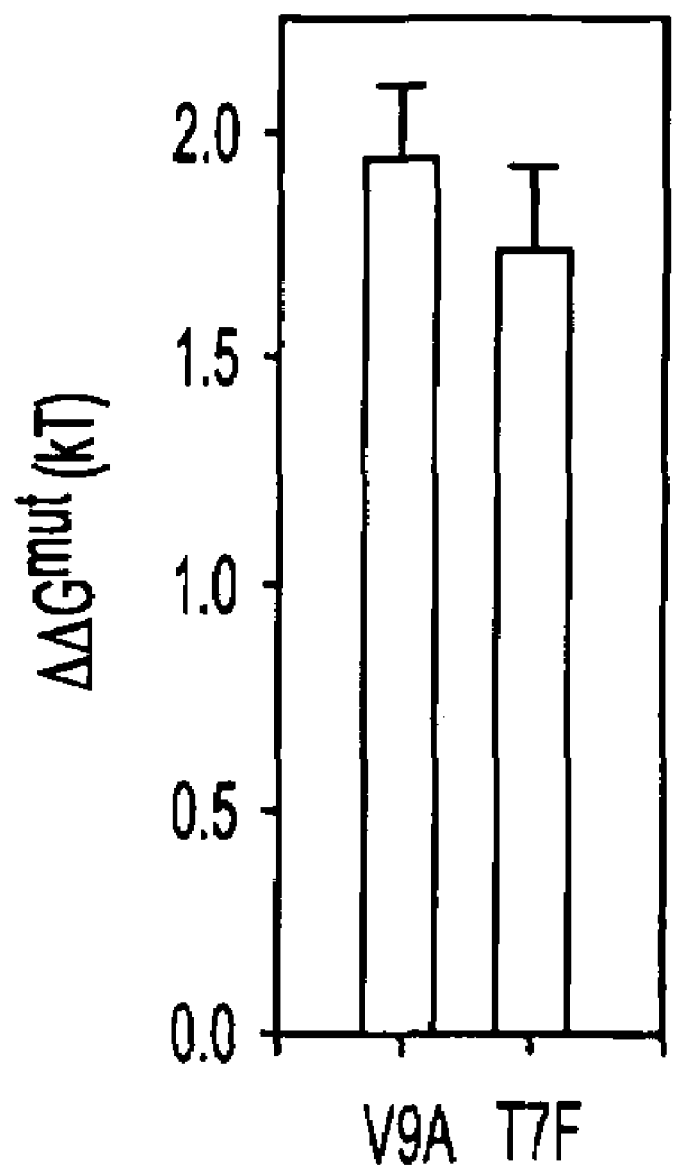

Using this assay, we measured coupling energies for a mutation at position 76 (H76Y) against mutations at a set of 14 PDZ domain positions and two peptide positions. The mutations chosen were designed to test a range of statistical couplings on the PDZ domain, including a set of sites that are not significantly statistically coupled. FIGS. 9–10 show that statistical coupling energies at sites, whether spatially near to, or distant from position 76 are in fact well correlated to the thermodynamic coupling through mutagenesis. Importantly, statistically uncoupled sites display mutational coupling energies near to noise. FIG. 11 shows a scatter plot of these data comparing coupling measured from statistical theory and from mutagenesis, indicating excellent reliability in the assignment of thermodynamic coupling. Thus, patterns of statistical energetic coupling for a protein site are likely to describe the thermodynamic energetic connectivity for that position.

The statistical analysis for perturbation at position 76 indicated that other binding site positions [positions 29 and 26] are energetically coupled, and suggested the possibility of propagated coupling through the substrate peptide (FIG. 8). Indeed, mutations at the peptide position directly interacting with PDZ position 76 (T7F), and at the position carrying the terminal carboxylate (V9A) are also thermodynamically coupled to the H76Y mutation.

Example 6

Applications to Non—Protein Biological Sequences

The inventive methods may be used to analyze biological sequences other than proteins. For example, $\Delta G^{stat}$ and $\Delta\Delta G^{ij,stat}$ may be calculated for polysaccharides, lipids, deoxyribonucleic acid (DNA, represented by A, C, G, and T bases), and ribonucleic acid sequences (RNA, represented by A, C, G, and U bases) to identify evolutionary conservation and interacting pairs of components. Any polymer of monomers may be analyzed with the inventive methods. Application of the inventive methods is not limited to biological sequences, as it may be applied to chemical polymers, drugs, and other compounds.

The inventive methods may also be used to analyze inter-protein (two proteins) interactions, as well as the intra-protein (one protein) interactions described in the Examples. The inventive methods may further be used to investigate drug-protein interactions, nucleic acid-protein interactions, and other chemical molecule-protein interactions.

Program Storage Device

It will be apparent to those of ordinary skill having the benefit of this disclosure that any of the foregoing variations may be implemented by programming one or more suitable general-purpose computers having appropriate hardware. The programming may be accomplished through the use of a program storage device readable by the computer and encoding a program of instructions executable by the computer for performing the operations described above. The program storage device may take the form of, e.g., one or more floppy disks; a CD ROM or other optical disk; a magnetic tape; a read-only memory chip (ROM); and other forms of the kind well-known in the art or subsequently developed. The program of instructions may be "object code," i.e., in binary form that is executable more-or-less directly by the computer; in "source code" that requires compilation or interpretation before execution; or in some intermediate form such as partially compiled code. The precise forms of the program storage device and of the encoding of instructions are immaterial here.

Function of Pathways Between Coupled Positions

The results of the examples set forth above facilitated the mapping of protein energetics. In addition, we have explored the biological roles for the pathways of energetic coupling. We did this by working with large alignments of functionally well-characterized protein families to identify coupled residues through statistical analysis of MSAs, and to determine that these represent the structural elements mediating function both in vitro and in vivo. We chose two well-known protein families, the p21$^{ras}$ family of GTPases and the hemoglobin family of oxygen carrying proteins, as model systems. Based on the success of our work in identifying coupled residues through statistical analysis, we hypothesized that, for signaling proteins, the prediction of positions for mutagenesis could be achieved because relatively subtle perturbations would disrupt the energetic connectivity and lead to large functional defects in vivo due to the uncoupling of signaling events. In other words, we believed that sequence-derived patterns of statistical coupling identified the structural elements of function in protein structure.

In the p21$^{ras}$ family, we found pathways of statistical connectivity that coupled the guanine nucleotide-binding pocket to the binding site for effector molecules. Our finding was consistent with the fact that this signaling protein family uses the exchange of GDP to GTP nucleotide as a switch for determining binding to effectors. We note that this is a functionally diverse family that shares the GTP switch mechanism as a strategy to regulate may biological processes. Defects in some of these, including $p_{21}^{ras}$, are associated with many human cancers. For the hemoglobin family, a classic model system for multi-subunit allostery, our statistical analysis using the methods described above revealed pathways of connectivity between pairs of heme groups in the tetrameric protein complex that were exactly consistent with experimentally established principles of oxygen binding allostery. Also, several well-known variants of hemoglobin isolated from human patients that show reduced or absent cooperativity of oxygen binding map to the positions predicted using our statistical analysis.

Remarkably, the sets of coupled residues in both the p21$^{ras}$ and hemoglobin families formed connected pathways in a state-dependent manner. Residues in the $p_{21}^{ras}$ family coupled to effector binding site positions were only contiguous when the bound nucleotide was GTP, a finding that implied nucleotide-dependent reorganization of thermodynamic connectivity in this protein family. Similarly, the coupled residues in the hemoglobin family were only connected in the de-oxy form (T-state), and demonstrated a discontinuous pattern in the oxygenated form (R-state). This feature was nicely consistent with the observations of Monod, Wyman, and Changeux who in their classic paper on protein allostery, suggested that allosteric ligands mediate "some kind of molecular transition which is induced or stabilized in the protein" (Monod, J. et al., *J. Mol. Biol.* 12: 88–118, 1965).

Based on our work, we suggest that the allosteric molecular transitions represent the relative stabilization of structural states that differ in the pattern of energetic connectivity on the protein, and these differences are the causal basis for the functional switching.

Mechanisms of Energetic Coupling

While the present statistical methods are useful in identifying couplings between positions in biological sequences (such as amino-acid positions in protein sequences), they do not by themselves reveal the physical mechanism of the energetic coupling. Nevertheless, the arrangement of coupled residues into ordered pathways through the cores of proteins suggests that the general mechanism of coupling may be simple mechanical compliance of the structure along the coupled pathways. In this view, a structural perturbation at one end of the pathway does not emanate uniformly through a protein; instead, much like fracture lines through many substances, the protein structure accommodates the perturbation along specific directions defined by the pattern of energetic coupling. Thus, much like in hydraulic systems, signals in proteins propagate efficiently and are not locally dissipated during signaling events. If correct, our hypothesis predicts that comparative high-resolution crystal structures of point mutants relative to wild-type protein may reveal pathways of anisotropic structural changes. Our hypothesis further predicts that the overlap in the structural changes of two mutations may reliably map those positions that energetically interact.

We chose the green fluorescent protein (GFP), a model system well suited for both energetic and structural studies, as an initial test case to develop the necessary structural techniques. Large-scale scanning mutagenesis of GFP revealed hot spots of interaction energy within the chromophore-binding pocket, and double mutant cycles showed specific cases of large and small energetic coupling. To assess the structural correlates of these thermodynamic phenomena, we solved the crystal structures of six GFP proteins representing two complete double mutant cycles and developed an atomic parameter ($\Delta\Delta_{struct}$, described below) that measured the coupled structural change of two perturbations. Specifically, we carried out the analysis of structural coupling for two cases of energetic coupling in GFP: (1) the interaction of mutation at position 145 (Y145C) with mutation at position 203 (T203C), and (2) the interaction of protonation of GFP (pH 8.5 to pH 5.5) with mutation at position 203 (T203C). These experiments revealed that (1) single mutations in fact induce structural changes along specific pathways in the protein and (2) energetic couplings quantitatively correlate with well-resolved structural interactions between mutations.

The principle and one implementation of our method are as follows. A crystal structure of a protein gives four values for each atom in the structure: the three spatial coordinates that give the atom's centroid position in space and one value termed the B-factor, which is related to standard deviation of the atom from its centroid. As used herein, the "centroid" means the center of mass of an atom. A single mutation on a protein may in principle produce structural changes that remain localized to the site of mutation or that may propagate to distant sites. To characterize the effects of a mutation at any given atom, we compared the position and B-factor of the atom in high-resolution crystal structures of the mutant and wild type protein, and calculated the following parameter representing the quantity of change:

$$\Delta_{struct} = \frac{|\vec{r}_{mut}|}{\sqrt{\sigma_{mut}^2 + \sigma_{wt}^2}},$$

where $|\vec{r}_{mut}|$ represents the magnitude of the vector connecting the position of the atom in the mutant structure and the position of the atom in the wild type structure, and $\sigma_{mut}$ and $\sigma_{wt}$ represent the standard deviations of the atom in the mutant and wild type structures, respectively. The standard deviations were calculated from the B-factors of each atom as described in Stroud and Fauman (*Protein Science* (1995) 4:2392–2404). This parameter ($\Delta_{struct}$) gave the quantity of structural change for each atom.

The structural coupling of two mutations is the degree to which the structural change induced by one mutation is different from that induced in the presence of another mutation. To determine this, we solved crystal structures of the wild-type protein, each single mutant protein (mutant 1 and mutant 2), and the double mutant protein. The solving of these crystals structures is well within the skill of one in the art. The following parameter then gave the quantity of structural coupling ($\Delta\Delta_{struct}$) due to the two mutations for each atom:

$$\Delta\Delta_{struct} = \frac{|\vec{r}_{mut1} - \vec{r}_{mut1|mut2}|}{\sqrt{\sigma_{wt}^2 + \sigma_{mut1}^2 + \sigma_{mut2}^2 + \sigma_{mut1,mut2}^2}},$$

where $\vec{r}_{mut1}$ represents the vector connecting the position of the atom in the structure of mutant 1 and the position of the atom in the wild type structure, and $\vec{r}_{mut1|mut2}$ represents the vector connecting the position of the atom in the structure of the double mutant (mut1,mut2) and the position of the atom in the structure of mutant 2. Here, $\sigma_{wt}$ represents the standard deviation of the atom in the wild-type protein; $\sigma_{mut1}$ represents the standard deviation of the atom in mutant 1; $\sigma_{mut2}$ represents the standard deviation of the atom in mutant 2; and $\sigma_{mut1,mut2}$ represents the standard deviation of the atom in the double mutant. These standard deviations were calculated from the B-factors of each atom as described in Stroud and Fauman (*Protein Science* (1995) 4:2392–2404).

Though the perturbation described above comprised mutagenesis, the present methods may be employed for all forms of perturbation. For example, other non-mutagenic perturbations include, but are not limited to, the binding of pharmacological agents, the binding of other proteins, or changes in pH that may alter the protonation of sites in proteins. In addition, it will be understood that as disclosed herein, the source of a perturbation is irrelevant for present purposes. In other words, perturbed biological sequences that exist in nature are as useful as those achieved through human intervention. Human intervention may effect changes through, for example, the binding of pharmacological agents or mutagenesis.

Our findings may be used to help facilitate the process of optimizing lead compounds during drug design by predicting which positions in a drug binding site act as structurally independent positions, and which act cooperatively with other positions. Such cooperative effects of protein sites may also be the basis for the development of drug resistance. For example, positions that are structurally coupled to drug binding sites represent potential sites for selection of mutations that reduce or eliminate the potency of the drug. The combined usage of our statistical algorithms for sequence analysis together with these crystallographic methods provides a method for prediction of the cooperative interactions at drug binding sites.

DNA Microarray Analysis

As explained above, the present methods are useful for analyzing non-protein biological sequences. For example, the present methods are useful for analyzing DNA microarray data, where the major current goal is to develop methods to identify the specific interaction of gene products during biological events. Present methods for this analysis typically involve the comparison of genome wide transcriptional changes before and after many perturbations to cells or animals and the clustering of similar patterns of transcriptional change. This work has helped to identify groups of genes that co-vary during many different biological processes and has set the standard for the primary mechanism of discovering relationships between genes.

An unrealized goal of microarray technology is the ability to map pathways of signaling in cells through the analysis of covariance in gene transcription due to genetic mutation. A single gene knockout shows changes in the expression of tens or hundreds of genes in comparison with wild type suggesting a combination of both local perturbation of a signaling pathway specific to the mutated gene and the propagated effect of the mutation. Also, in many cases the effect is small relative to noise. Prior methods have been unable to map the interaction of the gene of interest in its signaling pathway or identify the changes that are distantly correlated long-range effects of genetic mutation.

We extended our work to address this problem. Using the publicly available database of microarray data for the yeast mating pathway published by Rosetta Inpharmatics, we determined that the specific pathway of interaction of two gene mutations can be robustly and reliably identified through the non-additivity of their expression profiles.

The non-additivity of two perturbations in triggering gene expression changes was calculated in the following way. Each perturbation may cause the change in the expression of any other gene in the genome. In this regard, "perturbation" is a broad term, and may include a single gene mutation, multiple gene mutations, an applied pharmacological agent, or a disease state. The quantity of expression change for each gene in the genome due to a single perturbation is given by the fold change in the microarray hybridization signal for that gene. We calculated the coupling of two perturbations as the degree to which the fold change of expression of one gene was different in the presence of a second perturbation. To determine this, we obtained microarray data for four conditions: (a) the unperturbed "wild type" condition, (b) perturbation 1, (c) perturbation 2, and (d) the double perturbation of 1 and 2. The degree of coupling between perturbations 1 and 2 for each gene ($\Delta\Delta E$) is given by:

$$\Delta\Delta E = kT' \ln\left(\frac{f_1}{f_2}\right),$$

where $f_1$ is the fold effect of the gene due to perturbation 1 relative to wild type, and $f_2$ is the fold effect of the gene due to the combined perturbation of 1 and 2 relative to perturbation 2 alone. The calculation of this value for all genes in the genome gives the full analysis of genes responsible for the interaction of two perturbations. Similar to T* used herein, T', the "temperature" of the ensemble of this system, is related to the mean transition rates between states, but the energy unit, kT', in such a system is not necessarily related to that for conventional mechanical systems, or to kT* described above.

As in case of protein sites on a sequence alignment, this approach measures the interaction of two genes as the degree to which the expression changes due to mutation in the first are different when tried in the background of mutation in the second. Interestingly, this provides a quantitative measure of the interaction, and provides a list of genes that are responsible for the interaction. In the case of microarray analysis of mutations in the yeast mating pathway data, we were able to extract essentially the entire pathway of the mating factor through analysis of the non-additivity of two mutations (Rst1 and Rst2) in that pathway. In addition, the non-additivity analysis provided signal to noise in distinguishing genes known to be involved in this pathway from those not involved in this pathway.

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the methods described herein without departing from the concept, spirit and scope of the invention. All such similar substitutes and modifications apparent to those skilled in the art are deemed to be within the spirit, scope and concept of the invention.

REFERENCES

The following references, to the extent that they provide exemplary procedural or other details supplementary to those set forth herein, are specifically incorporated herein by reference.
1. U.S. Pat. No. 5,523,208 (issued Jun. 4, 1996)
2. Altschul, S. F. et al., *Nucl. Acids Res.*, 25: 3389–3402, 1997
3. Atwell, S. et al., *Science*, 278: 1125–1128, 1997
4. Bailey, T. L. and Gribskov, M., *Bioinformatics*, 14: 48–54, 1998
5. Bohm, G. and Jaenicke, R., *Protein Sci.*, 1: 1269–1278, 1992
6. Cabral, J. H. et al., *Nature*, 382: 649–652, 1996
7. Carter, P. J. et al., *Cell*, 38: 835–840, 1984
8. Clackson, T. and Wells, J. A., *Science*, 267: 383–386, 1995
9. Daniels, D. L. et al., *Nat. Struct. Biol.*, 5: 317–325, 1998
10. Doolittle, R. *Meth., Enzymol.*, 266, 1996
11. Doyle, D. A. et al., *Cell*, 85: 1067–1076, 1996
12. EGFP, Heim, R. and Tsien, R. Y., *Curr. Biol.*, 6: 178–181, 1996
13. Goldstein, S. A. et al., *Neuron*, 12: 1377–1388, 1994
14. Hedstrom, L., *Biol. Chem.*, 377: 465–470, 1996
15. Hedstrom, L. et al., *Science*, 255: 1249–1253, 1992
16. Hidalgo, P. and MacKinnon, R., *Science*, 268: 307–310, 1995
17. Holt, J. M. and Ackers, G. K., *FasebJ*, 9: 210–218, 1995
18. Hughey, R. and Krogh, A., *Comput. Appl. Biosci.*, 12: 95–107, 1996
19. Karlin, *Curr. Opin. Struct. Biol.*, 5: 360–371, 1995
20. Karlin, *Philos. Trans. R. Soc. Lond. B. Biol. Sci.*, 344: 391–402, 1994
21. Karlin, S. and Brendel, V., *Science*, 257: 39–49, 1992
22. Leluk, J., *Comput. Chem.*, 22(1):123–131, 1998
23. LiCata, V. J. and Ackers, G. K., *Biochemistry*, 34: 3133–3139, 1995
24. Lichtarge, O. et al., *J. Mol. Biol.*, 257: 342–358, 1996
25. Monod, J. et al., *J. Mol. Biol.*, 12: 88–118, 1965
26. Nicholls, A. et al., *Proteins*, 11: 281, 1999
27. Ortiz, A. R. et al., *Pac. Symp. Biocomput.*, 316–327, 1997)
28. Patten, P. A. et al., *Science*, 271: 1086–1091, 1996
29. Perona, J. J. et al., *Biochemistry*, 34: 1489–1499, 1995)
30. Perry, K. M. et al., *Biochem.*, 28: 7961–7968, 1989
31. Pettigrew, D. W. et al., *Proc. Natl. Acad. Sci., U.S.A.* 79: 1849–1853, 1982
32. Ponting, C. P. et al., *Bioessays*, 19: 469–479, 1997
33. Ranganathan, R., unpublished results
34. Ranganathan, R. et al., *Neuron*, 16: 131–139, 1996
35. Sambrook, J. et al. *Molecular Cloning: A Laboratory Manual*, 2$^{nd}$ Ed., Cold Spring Harbor, N.Y., 1989
36. Schreiber, G. and Fersht, A. R., *J. Mol. Biol.*, 248: 478–486, 1995
37. Songyang, Z. et al., *Science*, 275: 73–77, 1997
38. Stroud and Fauman, *Protein Science*, 4:2392–2404, 1995
39. Stampe, P. et al., *Biochemistry*, 33: 443–450, 1994
40. Sunyaev, S. R. et al., *Protein Eng.*, 12: 387–394, 1999
41. Thompson, et al., *Nuc. Acids Res.*, 22: 4673–4680, 1994
42. Tolman, R. C., *The Principles of Statistical Mechanics* (Dover Publications Inc., New York, 1938)
43. Turner, G. J. et al., *Proteins*, 14: 333–350, 1992
44. Vingron, M. and Waterman, M. S., *J. Mol. Biol.*, 235: 1–12, 1994
45. Wells, J. A., *Proc. Natl. Acad. Sci.*, 93: 1–6, 1996
46. Wells, J. A., *Biotechnol.*, 13: 647–651, 1995.

What is claimed is:

1. A method of identifying one or more positions in a protein family, the method comprising:
(a) accessing data representing a multiple sequence alignment (MSA) of a plurality of protein sequences; and
(b) identifying one or more evolutionarily conserved amino acid positions within the MSA using the following equation:

$$\Delta G_i^{stat} = kT^* \sqrt{\sum_x \left( \ln \frac{P_i^x}{P_{MSA}^x} \right)^2}$$

wherein:
i is a position in the MSA;
$\Delta G_i^{stat}$ is the conservation energy value for position i;
$P_i^x$ is the probability of amino acid x at position i;
$P_{MSA}^x$ is the probability of amino acid x in the MSA; and
kT* is an energy unit, where k is Boltzmann's constant.

2. The method of claim 1, wherein the method is executed using a machine.

3. A program storage device comprising machine readable instructions for performing the operations recited in claim 1.

4. The method of claim 1, further comprising generating a graphical image of one or more conservation energy values calculated using the equation.

5. The method of claim 1, wherein the data accessed comprises data from the PSD-95 (Postsynaptic density protein of Mr 95 kDa), Dlg (*Drosophila* Discs-Large protein) and ZO-1 (Zonula occludens protein 1) protein family.

6. The method of claim 1, wherein the data accessed comprises data from the p21$^{ras}$ protein family.

7. The method of claim 1, wherein the data accessed comprises data from the hemoglobin protein family.

8. A method of identifying one or more positions in a protein family, the method comprising:
(a) accessing data representing a multiple sequence alignment (MSA) of a plurality of protein sequences;
(b) calculating a conservation energy value for each position in the MSA using the following equation:

$$\Delta G_i^{stat} = kT^* \sqrt{\sum_x \left( \ln \frac{P_i^x}{P_{MSA}^x} \right)^2}$$

wherein:
i is a position in the MSA;
$\Delta G_i^{stat}$ is the conservation energy value for position i;
$P_i^x$ is the probability of amino acid x at position i;
$P_{MSA}^x$ is the probability of amino acid x in the MSA;
$kT^*$ is an energy unit, where k is Boltzmann's constant; and (c) identifying one or more positions within the MSA that have statistically significant conservation energy values.

9. The method of claim 8, wherein the method is executed using a machine.

10. The method of claim 8, further comprising generating a graphical image of the conservation energy values.

11. The method of claim 8, wherein the data accessed comprises data from the PSD-95 (Postsynaptic density protein of Mr 95 kDa), Dlg (Drosophila Discs-Large protein) and ZO-1 (Zonula occludens protein 1) protein family.

12. The method of claim 8, wherein the data accessed comprises data from the p21$^{ras}$ protein family.

13. The method of claim 8, wherein the data accessed comprises data from the hemoglobin protein family.

14. A program storage device comprising machine readable instructions for performing the method recited in claim 8.

* * * * *